US009310319B2

(12) United States Patent
Sato et al.

(10) Patent No.: US 9,310,319 B2
(45) Date of Patent: Apr. 12, 2016

(54) DEVICE FOR INSPECTING SUBSTRATE HAVING IRREGULAR ROUGH SURFACE AND INSPECTION METHOD USING SAME

(71) Applicant: JX NIPPON OIL & ENERGY CORPORATION, Tokyo (JP)

(72) Inventors: Yusuke Sato, Yokohama (JP); Suzushi Nishimura, Yokohama (JP)

(73) Assignee: JX NIPPON OIL & ENERGY CORPORATION, Tokyo (JP)

(*) Notice: Subject to any disclaimer, the term of this patent is extended or adjusted under 35 U.S.C. 154(b) by 0 days.

(21) Appl. No.: 14/667,159

(22) Filed: Mar. 24, 2015

(65) Prior Publication Data

US 2015/0192529 A1    Jul. 9, 2015

Related U.S. Application Data

(63) Continuation of application No. PCT/JP2013/074827, filed on Sep. 13, 2013.

(30) Foreign Application Priority Data

Sep. 28, 2012   (JP) .................................. 2012-217348

(51) Int. Cl.
| | |
|---|---|
| G01N 21/956 | (2006.01) |
| G01N 21/47 | (2006.01) |
| H01L 21/66 | (2006.01) |
| H01L 51/56 | (2006.01) |
| G01N 21/88 | (2006.01) |
| H01L 51/52 | (2006.01) |

(52) U.S. Cl.
CPC .......... *G01N 21/956* (2013.01); *G01N 21/4738* (2013.01); *G01N 21/88* (2013.01); *G01N 2201/062* (2013.01); *H01L 22/12* (2013.01); *H01L 51/5268* (2013.01); *H01L 51/56* (2013.01)

(58) Field of Classification Search
None
See application file for complete search history.

(56) References Cited

U.S. PATENT DOCUMENTS

| | | | | |
|---|---|---|---|---|
| 7,315,366 B2* | 1/2008 | Hamamatsu | ....... | G01N 21/9501 356/237.2 |
| 8,638,430 B2* | 1/2014 | Sasazawa | ......... | G01N 21/95692 356/237.1 |

(Continued)

FOREIGN PATENT DOCUMENTS

| | | |
|---|---|---|
| JP | 2006-046941 A | 2/2006 |
| JP | 2006-236748 A | 9/2006 |

(Continued)

OTHER PUBLICATIONS

Dec. 17, 2013 International Search Report issued in International Application No. PCT/JP2013/074827.

(Continued)

*Primary Examiner* — Seahvosh Nikmanesh
(74) *Attorney, Agent, or Firm* — Oliff PLC

(57) ABSTRACT

A substrate inspection apparatus for inspecting a substrate having an irregular concave-convex surface for scattering lights, comprises a first irradiation system which irradiates the substrate with a first detection light; a first detection system which detects any luminance unevenness from the entire concave-convex surface of the substrate irradiated with the first detection light; a second irradiation system which irradiates the substrate with a second detection light having a wavelength different from that of the first detection light; and a second detection system which detects any defect of the concave-convex surface of the substrate irradiated with the second detection light. The luminance unevenness and a pattern defect of the substrate having the irregular concave-convex surface can be inspected effectively at low cost.

22 Claims, 13 Drawing Sheets

(56) References Cited

U.S. PATENT DOCUMENTS

| | | |
|---|---|---|
| 2002/0122174 A1 | 9/2002 | Hamamatsu et al. |
| 2012/0132897 A1 | 5/2012 | Seki et al. |
| 2013/0299796 A1 | 11/2013 | Masuyama et al. |

FOREIGN PATENT DOCUMENTS

| | | |
|---|---|---|
| JP | 2011-203223 A | 10/2011 |
| WO | 2011/007878 A1 | 1/2011 |
| WO | 2012/096368 A1 | 7/2012 |

OTHER PUBLICATIONS

Oct. 21, 2014 Office Action issued in Japanese Application No. 2014-538396.

Mar. 31, 2015 International Preliminary Report on Patentability issued in International Application No. PCT/JP2013/074827.

Jan. 7, 2016 Office Action issued in Canadian Application No. 2,886,007.

* cited by examiner

DEVICE FOR INSPECTING SUBSTRATE HAVING IRREGULAR ROUGH SURFACE AND INSPECTION METHOD USING SAME

CROSS REFERENCE TO RELATED APPLICATION

This application is a continuation application of International Patent Application No. PCT/JP2013/074827 filed on Sep. 13, 2013 claiming the benefit of priority of Japanese Patent Application No. 2012-217348 filed on Sep. 28, 2012. The contents of International Patent Application No. PCT/JP2013/074827 and Japanese Patent Application No. 2012-217348 are incorporated herein by reference in their entities.

BACKGROUND OF THE INVENTION

1. Field of the Invention

The present invention relates to an inspection apparatus for inspecting a substrate having irregular concavities and convexities (unevennesses, or protrusions and recesses) used to produce, for example, an organic electroluminescent element, and an inspection method based on the use of the same.

2. Description of the Related Art

An organic electroluminescent element (or referred to as "organic light emitting diode" as well, hereinafter referred to as "organic EL element") is known as a self-luminescent (self-light emitting) type display element. The organic EL element has higher visibility as compared with the liquid crystal element, and any backlight is unnecessary therefor. Therefore, it is possible to realize the light weight. In view of the above, research and development are vigorously performed in relation to the organic EL element as a next-generation display element.

In the organic EL element, the positive holes introduced from a hole injection layer and the electrons introduced from an electron injection layer are carried to a light emitting layer respectively, they are recombined on organic molecules in the light emitting layer to excite the organic molecules, and thus the light is released thereby. Therefore, in order to use the organic EL element as a display apparatus, it is necessary that the light coming from the light emitting layer should be efficiently extracted or taken out from the element surface. For this purpose, a technique is known as described, for example, in JP2006-236748A, in which a diffraction grating substrate is provided on a light extraction surface of the organic EL element.

In the meantime, the present applicant has disclosed the following method in WO2011/007878A1. That is, a solution, which is obtained by dissolving, in a solvent, a block copolymer that fulfills a predetermined condition, is applied onto a base member, and drying is performed to form a micro phase separation structure of the block copolymer, thereby obtaining a master block (mold) (metal substrate) in which a fine (minute) and irregular concave-convex pattern is formed. According to this method, it is possible to obtain the master block usable for the nano-imprint and the like by using a self-organizing phenomenon of the block copolymer. A mixture of a silicone-based polymer and a curing agent is dropped onto the obtained master block and then cured to obtain a transferred pattern. Then, a glass substrate coated with a curable resin is pressed to (against) the transferred pattern, and the curable resin is cured by irradiation with an ultraviolet light. In this way, a diffraction grating in which the transferred pattern is duplicated is manufactured. It has been confirmed that an organic EL element obtained by stacking a transparent electrode, an organic layer, and a metal electrode on the diffraction grating has sufficiently high light emission efficiency, sufficiently high level of external extraction efficiency, while having sufficiently low wavelength-dependence of light emission, sufficiently low directivity of light emission, and sufficiently high power efficiency.

Even in the case of the organic EL element which uses the diffraction grating produced in accordance with WO2011/007878A1 as described above, when the organic EL element is used as a display device or an illumination device for a mobile phone or a television screen, it is desirable that the light is radiated at a uniform luminance from the entire display surface. Further, it is necessary to avoid the appearance of pattern defect which causes the appearance of intensity fluctuation of light (strong light and weak light) at any minute portion of the display surface. For this reason, it is necessary to confirm the fact that the irradiation from the organic EL element is uniform, i.e., the fact that the luminance unevenness (uneven luminance) is within an allowable range and the fact that the brightness or darkness does not arise at any minute portion, after the completion of the organic EL element. However, if it is judged that the luminance unevenness of the completed organic EL element or the brightness or darkness of the minute portion is without the allowable range, then the organic EL element is regarded as a defective product, and the step of stacking the multiple layers on the diffraction grating as described above becomes wasteful. In particular, the stacking of, for example, the transparent electrode, the organic layer, and the metal electrode is the laborious process in which the production cost is expensive. It is strongly demanded that the defective product as described above is reduced to improve the yield and curtail the wasteful use of the material and the production cost.

In order to evaluate the luminance unevenness, it is necessary that the inspection should be performed simultaneously for a relatively large area. On the contrary, in order to inspect the pattern defect which causes the light intensity fluctuation of the minute portion, the inspection is performed in a relatively narrow field. Further, it is necessary that the former inspection should not be affected by the latter inspection. Therefore, it is necessary that the luminance unevenness and the pattern defect should be inspected and evaluated efficiently and independently. Furthermore, the substrate, which is the inspection objective, is produced by performing the transfer process including, for example, the nano-imprinting. Therefore, it is desirable the luminance unevenness and the pattern defect are also inspected for that the metal mold as the transfer base and the light transmissive mother substrate generated therefrom. For the way of use as described above, it is desirable to adopt an inspection apparatus which can inspect not only the light transmissive substrate but also the light non-transmissive substrate. Moreover, the device, which includes, for example, a sensor for measuring the uniformity of light and the luminance from the display surface having a large area (areal size), is relatively expensive.

SUMMARY OF THE INVENTION

In view of the above, an object of the present invention is to provide an inspection apparatus and an inspection method which make it possible to efficiently inspect, at low cost, both of the luminance unevenness and the local pattern defect of a substrate having an irregular concave-convex surface. Another object of the present invention is to provide an inspection apparatus and an inspection method which make it possible to inspect both of the luminance unevenness and the pattern defect of any one of a light transmissive substrate and a light non-transmissive substrate obtained when a substrate having an irregular concave-convex surface is produced by performing a transfer process.

According to a first aspect of the present invention, there is provided a substrate inspection apparatus for inspecting a substrate having an irregular concave-convex surface for scattering lights, comprising:

a first irradiation system which irradiates the substrate with a first detection light;

a first detection system which detects any luminance unevenness from the entire concave-convex surface of the substrate irradiated with the first detection light;

a second irradiation system which irradiates the substrate with a second detection light having a wavelength different from that of the first detection light; and a second detection system which detects a pattern defect of the concave-convex surface of the substrate irradiated with the second detection light.

In the substrate inspection apparatus of the present invention, the first detection light may be a blue light, and the second detection light may be a white light.

In the substrate inspection apparatus of the present invention, the first irradiation system may include a transmitting light illumination for illuminating a light transmissive substrate and a non-transmitting light illumination for illuminating a light non-transmissive substrate, and the second irradiation system may include a transmitting light illumination for illuminating the light transmissive substrate and a non-transmitting light illumination for illuminating the light non-transmissive substrate. Further, the non-transmitting light illumination of the first irradiation system and the non-transmitting light illumination of the second irradiation system may irradiate the irregular concave-convex surface of the substrate, and the transmitting light illumination of the first irradiation system and the transmitting light illumination of the second irradiation system may irradiate the irregular concave-convex surface of the substrate from a surface disposed on a side opposite to the irregular concave-convex surface of the substrate.

In the substrate inspection apparatus of the present invention, the first detection system may include a camera which detects the light coming from the light transmissive substrate illuminated with the transmitting light illumination of the first irradiation system and the light coming from the light non-transmissive substrate illuminated with the non-transmitting light illumination of the first irradiation system. Further, the second detection system may include a camera which detects the light coming from the light transmissive substrate illuminated with the transmitting light illumination of the second irradiation system and the light coming from the light non-transmissive substrate illuminated with the non-transmitting light illumination of the second irradiation system. A resolution of the camera of the second detection system may be higher than a resolution of the camera of the first detection system.

In the substrate inspection apparatus of the present invention, the camera of the second detection system may include a plurality of cameras which detect divided areas of the substrate respectively.

In the substrate inspection apparatus of the present invention, the first irradiation system and the second irradiation system may be line-shaped illuminations, and the apparatus may further comprise a substrate transport system which transports the substrate in a direction perpendicular to a direction in which the line-shaped illuminations extend.

The substrate inspection apparatus of the present invention may further comprise a control system which controls the substrate transport system, the first irradiation system, the second irradiation system, the first detection system, and the second detection system, wherein the control system can detect the pattern defect of the concave-convex surface when the substrate is moved by the substrate transport system in one direction with respect to the first irradiation system, the second irradiation system, the first detection system, and the second detection system, and the control system can detect the luminance unevenness when the substrate is moved in a direction opposite to the one direction with respect to the first irradiation system, the second irradiation system, the first detection system, and the second detection system. Further, the control system may judge whether or not the pattern defect of the concave-convex surface and the luminance unevenness are within predetermined allowable ranges.

According to a second aspect of the present invention, there is provided an inspection method for inspecting a light non-transmissive substrate having an irregular concave-convex surface for scattering lights and a light transmissive substrate having an irregular concave-convex surface for scattering lights, the inspection method comprising:

transporting the substrate with respect to a first detection system which detects any luminance unevenness from the entire concave-convex surface of the substrate and a second detector system which detects a pattern defect of the concave-convex surface of the substrate;

irradiating the concave-convex surface of the substrate with a first detection light to detect the light coming from the concave-convex surface by the first detection system, and irradiating the concave-convex surface of the substrate with a second detection light having a wavelength different from that of the first detection light to detect the light coming from the concave-convex surface by the second detection system, when the light non-transmissive substrate is transported; and irradiating the irregular concave-convex surface of the substrate with the first detection light from a surface of the light transmissive substrate disposed on a side opposite to the concave-convex surface to detect the light coming from the concave-convex surface by the first detection system, and irradiating the irregular concave-convex surface of the substrate with the second detection light from the surface of the light transmissive substrate disposed on the opposite side to detect the light coming from the concave-convex surface by the second detection system, when the light transmissive substrate is transported.

In the substrate inspection method of the present invention, the first detection light may be a blue light, and the second detection light may be a white light.

In the substrate inspection method of the present invention, each of the first detection light and the second detection light may be irradiated by a line-shaped illumination extending in a predetermined direction, and the substrate may be transported in a direction perpendicular to the direction in which the line-shaped illumination extends.

In the substrate inspection method of the present invention, the pattern defect of the concave-convex surface of the substrate may be detected when the substrate is moved in one direction with respect to the first detection system and the second detection system, and the luminance unevenness may be detected when the substrate is moved in a direction opposite to the one direction with respect to the first detection system and the second detection system.

The substrate inspection method of the present invention may further comprise judging whether or not the pattern defect of the concave-convex surface and the luminance unevenness are within predetermined allowable ranges.

According to a third aspect of the present invention, there is provided a substrate production method for producing a substrate having an irregular concave-convex surface for scattering lights, comprising:

preparing the substrate having the irregular concave-convex surface; and inspecting the substrate having the irregular concave-convex surface by using the substrate inspection method as defined in the first aspect of the present invention.

In the substrate production method of the present invention, the preparation of the substrate having the irregular concave-convex surface may comprise preparing a light non-transmissive substrate having an irregular concave-convex pattern, and transferring the irregular concave-convex pattern of the light non-transmissive substrate.

In the substrate production method of the present invention, the preparation of the substrate having the irregular concave-convex surface may comprise utilizing phase separation of a block copolymer.

In the substrate production method of the present invention, the irregular concave-convex surface may be formed of a metal, resin, or sol-gel material.

According to a fourth aspect of the present invention, there is provided a method for producing an organic EL element, comprising preparing a diffraction grating substrate having a concave-convex surface by using the substrate production method as defined in the third aspect of the present invention, and successively stacking a transparent electrode, an organic layer, and a metal electrode on the concave-convex surface of the diffraction grating substrate to produce the organic EL element.

In the method for producing the organic EL element of the present invention, the organic EL element may be produced by successively stacking the transparent electrode, the organic layer, and the metal electrode on the concave-convex surface of the diffraction grating substrate having the luminance unevenness within a predetermined allowable range and the pattern defect within a predetermined allowable range only when it is judged that the luminance unevenness and the pattern defect of the prepared diffraction grating substrate are within the predetermined allowable ranges.

According to the substrate inspection apparatus and the substrate inspection method of the present invention, the substrate having the irregular concave-convex surface to be used for the element such as the organic EL element or the like can be efficiently produced, while effectively inspecting the luminance unevenness and the pattern defect of the substrate as described above. According to the method for producing the organic EL element of the present invention, the organic EL element can be produced at a high throughput by correlating the characteristic of the luminance unevenness in relation to the organic EL element and the substrate having the irregular concave-convex surface to be used therefor. In particular, the occurrence of the luminance unevenness and the pattern defect of the finished product can be predicted and the finished product can be evaluated at the stage of production of the substrate. Therefore, the organic EL element having the uniform illuminance can be produced more reliably by using the substrate which is judged to be acceptable in the judgment or examination of the luminance unevenness and the pattern defect. Further, even when the uniformity of the illuminance of the organic EL element is defective (luminance unevenness) or even when the local light emission or the light reduction (extinction) arises, then it is possible to know whether any defective product is appeared either at the stage of formation of the substrate or at the stage of formation of the element itself. Therefore, it is possible to quickly respond to such a situation.

DESCRIPTION OF THE PREFERRED EMBODIMENTS

An explanation will be made in detail below with reference to the drawings about preferred embodiments of the substrate inspection apparatus according to the present invention and the inspection method based on the use of the same. The inspection apparatus and the inspection method of the present invention detect the luminance unevenness and the defect of the concave-convex pattern of the substrate having the irregular concave-convex surface.

<Outline of Inspection Method>

Figure 1:
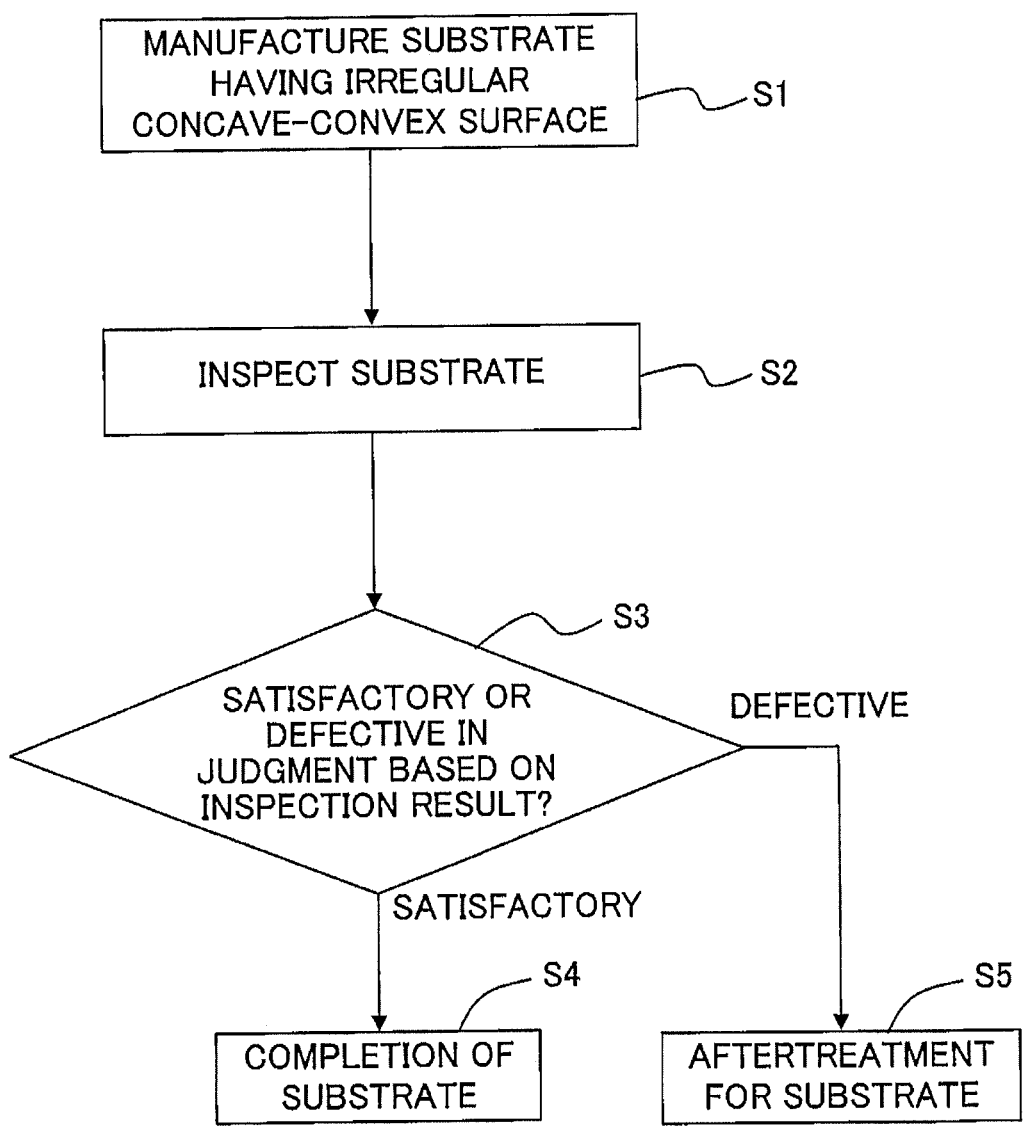
FIG. 1 shows a flow chart illustrating a substrate inspection method of the present invention.

The outline of the inspection method of the present invention will be explained in accordance with a flow chart shown in FIG. 1. At first, a substrate having an irregular concave-convex surface is manufactured or prepared (S1). In this context, the term "substrate having the irregular concave-convex surface" means the substrate in which the concave-convex pattern formed on the substrate has no regularity, especially the substrate in which the pitches of concavities and convexities are not uniform and no directivity is provided in relation to the directions of the concavities and convexities. The light, which is scattered and/or diffracted from the substrate as described above, is not the light having either single wavelength or narrow band wavelengths, but the light has a relatively wide wavelength band. The scattered light and/or the diffracted light has no directivity, and the light is directed in all directions. However, the "substrate having the irregular concave-convex surface" described above includes such a pseudo-periodic structure that a Fourier transform image, which is obtained by applying the two-dimensional high speed Fourier transform process to a concavity-convexity analysis image obtained by analyzing the shapes of the surface concavities and convexities, exhibits a circular or annular motif or marking (pattern), i.e., a distribution of the pitches of concavities and convexities is provided although no directivity is provided for the directions of the concavities and convexities. Therefore, the substrate, which has the pseudo-periodic structure as described above, is preferred for the diffraction substrate to be used, for example, for the surface light emission element such as the organic EL element, provided that the distribution of the pitches of concavities and convexities causes the diffraction of the visible ray. On the other hand, any substrate, which is formed by arranging all of recording tracks (grooves) in an identical direction at an identical pitch as exemplified by the optical recording medium and the magnetic recording medium, does not fall under the "substrate having the irregular concave-convex surface" as referred to in this patent application. Details of the steps of manufacturing the substrate having the irregular concave-convex surface will be described later on.

Subsequently, the substrate having the irregular concave-convex surface is inspected for the luminance unevenness of the substrate surface and the minute defect (for example, pattern defect, foreign matter, scratch) in accordance with the inspection step as described later on (S2). Further, the judgment is performed in accordance with the judging step as described later on about whether or not the substrate has the uniform luminance distribution and whether or not the minute defect is within the allowable range, on the basis of the inspection result (S3). If the substrate has the uniform luminance distribution and the detected minute defect is within the allowable range, then the substrate is regarded as a finished product, and the substrate is used for the process to be performed thereafter including, for example, the production of the organic EL (S4). If it is judged that the substrate does not have the uniform luminance distribution or the minute defect is without the allowable range, then the aftertreatment is applied in accordance with the aftertreatment step as described later on (S5).

<Inspection Apparatus>

Figure 2A:
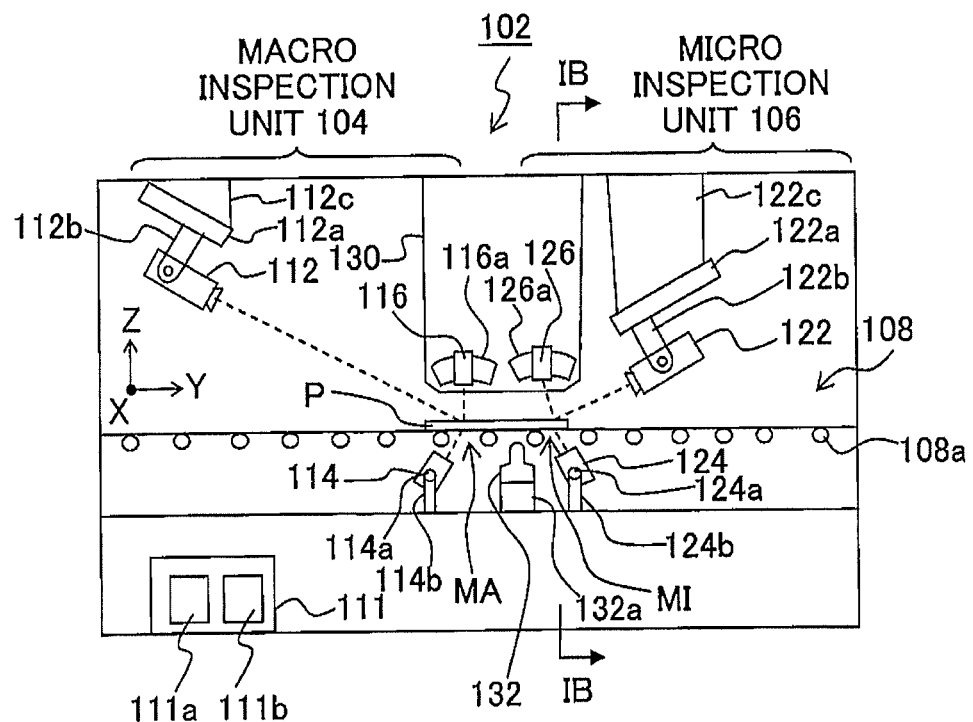
FIG. 2A schematically shows a schematic side view of a substrate inspection apparatus of the present invention.

The substrate inspection apparatus according to the present invention will be explained with reference to FIGS. 2 to 4. An inspection apparatus 102 shown in FIG. 2A mainly comprises, a transport system 108 which transports the substrate P from the upstream side to the downstream side in the transport direction (arrow Y in the drawing), a macro inspection unit 104, a micro inspection unit 106 which is provided on the downstream side as compared with the macro inspection unit 104, and a control unit 111 therefor. In this specification, the transport direction of the inspection apparatus 102 is designated as "Y direction", the direction parallel to the substrate surface and perpendicular to the transport direction is designated as "X direction", and the height direction perpendicular to the substrate surface is designated as "Z direction". The transport system 108 is a conveyer in which a plurality of rollers 108 are arranged in the transport direction. Some of the rollers 108a are driving rollers connected to a rotary driving source (not shown), and the substrate P is moved from the upstream side to the downstream side in the transport direction on the rollers 108a. A macro inspection position MA and a micro inspection position MI exist approximately at the center in the transport direction of the transport system 108. The method for transporting the substrate is not limited to the transport based on the rollers. It is also allowable to perform, for example, the transport based on a linear motor.

The macro inspection unit 104 is the unit for inspecting the luminance unevenness of the entire surface of the substrate P transported by the transport system 108. The macro inspection unit 104 mainly comprises a transmitting light illumination for macro 114 and a reflecting light (non-transmitting light) illumination for macro 116 which serve as an illumination system for macro (first irradiation system), and a macro camera 112 which serves as a macro detection system (first detection system). The detection objective of the macro detection system is the area (region) having an areal size of not less than 0.1 mm$^2$.

Figure 3A:
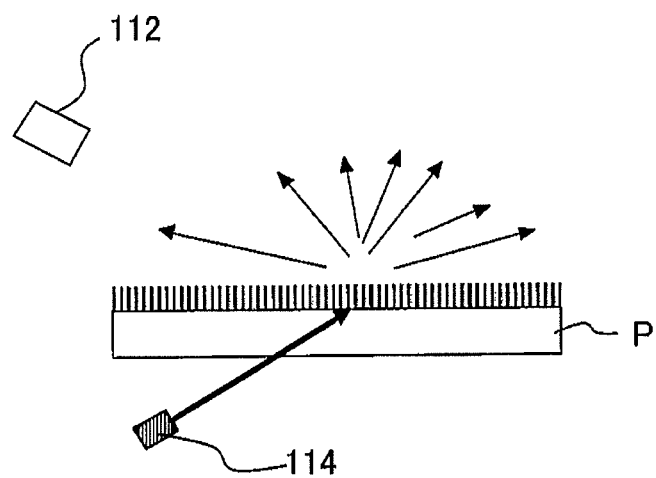
FIG. 3A conceptually shows a situation provided when a light transmissive substrate is inspected by using a transmitting illumination for macro (for macro inspection), and FIG. 3B conceptually shows a situation provided when a light non-transmissive substrate is inspected by using a non-transmitting illumination for macro (for micro inspection).

The transmitting light illumination for macro 114 is the illumination which is used to inspect the light transmissive substrate, and the transmitting light illumination for macro 114 is provided under or below the transport system 108. In this embodiment, a blue LED line-shaped illumination, in which a plurality of blue LEDs for emitting the light (first detection light) having a wavelength of 400 nm to 500 nm are embedded in a frame in an array form in the X direction, is used herein as the transmitting light illumination for macro 114. The use of the blue LED line-shaped illumination is advantageous in that i) the observation range can be uniformly illuminated, ii) the unevenness appears clearly, and iii) any influence is hardly exerted by any foreign matter. In view of the advantages as described above as well, it is preferable that the transmitting light illumination for macro 114 is the blue LED line-shaped illumination even when the substrate material is any one of film, glass, and metal. The transmitting light illumination for macro 114 is attached rotatably about the center of a rotary shaft 114a on a support base 114b so that the angle of incidence of the illumination light can be regulated with respect to the substrate P (or a part thereof) existing at the inspection position MA. As shown in FIG. 3A, the transmitting light illumination for macro 114 irradiates, with the light, the back surface of the substrate P existing at the inspection position MA, i.e., the surface on which the concave-convex structure is not formed. The light, which comes into the inside of the substrate P, is scattered and diffracted by the concave-convex pattern on the surface of the substrate P.

The scattered and diffracted light, which comes from the concave-convex structure, is received by the macro camera 112 which is installed over or above the transport system 108 on the upstream side in the transport direction as compared with the light irradiation unit. It is allowable that the macro camera 112 is an arbitrary image pickup element provided that the element can receive the scattered light and the diffracted light at the inspection position MA. A line sensor camera, which continuously photographs or picks up the one-dimensional image when the substrate P passes over the inspection position MA, is preferably used. When the line sensor camera is used, the scattered and diffracted lights, which come from the substrate P, can be always picked up at an identical angle. Note that the number of pixels of the image pickup element is preferably at least not less than 30. For example, it is possible to use a CCD camera of 80 μm/pixel. In general, the macro camera 112 is arranged at the position at which the primary diffracted light coming from the concave-convex pattern existing at the inspection position MA can be received. The macro camera 112 is attached to a movement stage 112a by the aid of an arm 112b having a rotary shaft. The movement stage 112a is slidably movable on a stage base 112c. The macro camera 112 can be moved in the X direction and the optical axis direction of the macro camera 112. Further, it is possible to change the angle of the optical axis of the macro camera 112 (receiving angle) by means of the rotary shaft of the arm 112b. Note that if a plurality of macro cameras 112 are provided, then not only the influence, which is exerted, for example, by the sensitivity error and the focal point adjustment among the cameras, appears, but it also becomes necessary to combine the data of the respective cameras with each other. In this case, the data processing becomes complicated. Therefore, it is desirable to perform the inspection by using one macro camera 112.

Figure 3B:
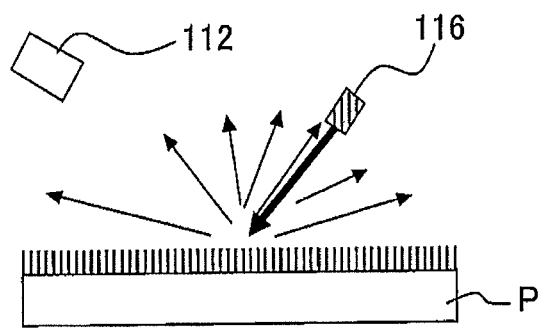

The non-transmitting light illumination for macro 116 is the illumination which is used to inspect the non-transmissive substrate. The non-transmitting light illumination for macro 116 is provided on a support base 130 disposed over or above the inspection position MA over or above the transport system 108. In this embodiment, a line-shaped illumination, in which LEDs for emitting the light having a wavelength of 400 nm to 500 nm are embedded in an array form in the X direction, is used as the non-transmitting light illumination for macro 116. The non-transmitting light illumination for macro 116 is provided slidably on a guide 116a so that the position and the angle of light irradiation can be regulated. As shown in FIG. 3B, the non-transmitting light illumination for macro 116 irradiates, with the light, the surface of the substrate P existing at the macro detection position MA, i.e., the surface on which the concave-convex pattern is formed, and the reflected light coming from the surface of the substrate P is scattered and diffracted by the concave-convex structure of the surface of the substrate P. The scattered light and the diffracted light coming from the concave-convex structure are received by the macro camera 112. As described above, even when the transported substrate is either light transmissive or non-transmissive, the macro inspection unit 104 can inspect any substrate by properly using the illumination systems. That is, the macro inspection unit 104 makes it possible to perform the both types of macro inspection of the light transmissive substrate and the light non-transmissive substrate, i.e., the inspection of the luminance unevenness in spite of the simple structure by using the two illumination systems and the macro camera commonly used therefor.

Figure 2B:
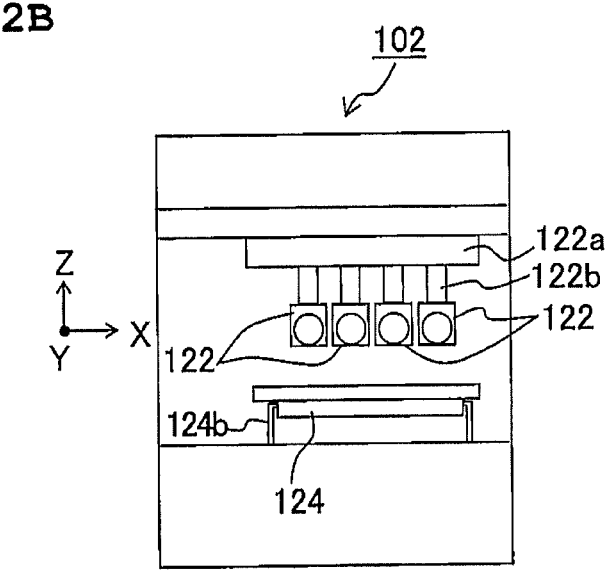
FIG. 2B shows a schematic sectional view as viewed in a direction of IB-IB shown in FIG. 2A.

The micro inspection unit 106 is the unit which inspects the pattern defect of the substrate P transported by the transport system 108, i.e., for example, the minute defect of the concave-convex structure for forming the pattern, the foreign matter adhered to the substrate P, and the scratch originating from the steps. The micro inspection unit 106 comprises a transmitting light illumination for micro 124 and a non-transmitting light illumination for micro 126 which serve as an illumination system for micro (second irradiation system), and micro cameras 122 which serve as a detection system for micro (second detection system). As shown in FIG. 2B, the four micro cameras 122 are arranged in the X direction. When the plurality of micro cameras 122 are aligned as described above, then the entire area of the inspection objective can be thereby inspected by means of one scanning, and the productivity can be improved by shortening the inspection tact. The detection objective of the micro detection system is the area having an areal size of 1 $\mu m^2$ to 25 $mm^2$.

The transmitting light illumination for micro 124 is the illumination which is used to inspect the light transmissive substrate, and the transmitting light illumination for micro 124 is provided under or below the transport system 108. In this embodiment, a line-shaped illumination, in which LEDs for emitting the light (second detection light) having a wavelength of 400 nm to 800 nm are embedded in a frame in an array form in the X direction, is used for the transmitting light illumination for micro 124. In particular, in order to obtain the sufficient light amount and perform the inspection highly accurately, it is preferable to use a high luminance white line illumination. The transmitting light illumination for micro 124 is attached rotatably about the center of a rotary shaft 124a on a support base 124b so that the micro inspection position MI and the angle of incidence of the illumination light with respect to the substrate P can be regulated. The transmitting light illumination for micro 124 irradiates, with the light, the back surface of the substrate P, i.e., the surface on which the concave-convex structure is not formed, in the same manner as the case of the transmitting light illumination for macro shown in FIG. 3A. The light, which comes into the inside of the substrate P, is scattered and diffracted by the concave-convex pattern on the surface of the substrate P. In any one of the transmitting light illumination for micro and the transmitting light illumination for macro, it is preferable that the illumination light is allowed to come at an angle of incidence of 20° to 60° with respect to the normal line of the substrate from the side on which the concavities and convexities of the substrate do not exist. If the substrate is irradiated from the concave-convex surface, then the light, which is diffracted and scattered by the surface (concave-convex surface), is reflected by the opposite surface (surface having no concavity and convexity), and hence any vivid image is hardly obtained. If the light is allowed to come at an angle lower than 20°, then the effect of diffraction and scattering, which is to be obtained by the concavities and convexities, is weakened, and it is impossible to obtain any sufficient light amount. If the light is allowed to come at an angle higher than 60°, it is impossible to obtain any sufficient light amount on account of the loss caused by the reflection. The preferred range of the angle of incidence also holds similarly for the non-transmitting light illumination for micro and the non-transmitting light illumination for macro.

The scattered and diffracted lights, which come from the concave-convex structure, are received by the micro cameras 122 which are installed over or above the transport system 108 on the downstream side in the transport direction from the transmitting light illumination 124. The micro camera detects the relatively narrow range at a high resolution. Therefore, it is preferable that the pixel size is 1 μm to 50 μm. If the pixel size is below 1 μm, any clear image is not obtained due to the insufficient light amount in some cases. In other cases, the depth of focus becomes shallow, and the image is blurred by any slight undulation and/or any vibration caused during the transport. If the pixel size exceeds 50 µm, it is feared that any minute defect cannot be detected. For example, it is possible to use a CCD camera adjusted to provide 15 µm/pixel. In general, the micro camera 122 is arranged at the position at which the primary diffracted light coming from the concave-convex pattern can be received. The micro camera 122 is attached to a movement stage 122a by the aid of an arm 122b having a rotary shaft. The movement stage 122a is slidably movable on a stage base 122c. Accordingly, the micro camera 122 can be moved in the X direction and the optical axis direction of the micro camera 122. Further, it is possible to change the inclination of the optical axis (light receiving angle) of the micro camera 122 by means of the rotary shaft of the arm 122b.

The non-transmitting light illumination for micro 126 is the illumination which is used to inspect the non-transmissive substrate. The non-transmitting light illumination for micro 126 is provided on the support base 130 disposed over or above the inspection position MA over or above the transport system 108. In this embodiment, a line-shaped illumination, in which LEDs for emitting the light having a wavelength of 400 nm to 800 nm are embedded in an array form in the X direction, is used for the non-transmitting light illumination for micro 126. The non-transmitting light illumination for micro 126 is provided slidably on a guide 126a so that the position and the angle for light irradiation can be regulated. The non-transmitting light illumination for micro 126 irradiates, with the light, the surface of the substrate P, i.e., the surface on which the concave-convex pattern is formed, and the scattering and the diffraction are caused by the concave-convex structure of the surface of the substrate P, in the same manner as the non-transmitting light illumination for macro 116 shown in FIG. 3B. The scattered and diffracted lights (reflected light) coming from the concave-convex structure are received by the micro cameras 122.

It is preferable that any one of the cameras of the micro inspection unit 106 and the macro inspection unit 104 is installed on the side of the concave-convex surface of the substrate. Further, it is preferable that the image pickup direction generally resides in the position at which the primary diffracted light coming from the concave-convex pattern can be received, i.e., at 40° to 80° from the normal line direction of the substrate. If the image pickup is performed at an angle lower than 40°, there is such a tendency that the effect of diffraction and scattering brought about by the concavities and convexities is weakened, and it is impossible to obtain any sufficient light amount. If the image pickup is performed at an angle higher than 80°, there is such a tendency that the effect of diffraction and scattering brought about by the concavities and convexities is weakened, and it is impossible to obtain any sufficient light amount.

As described above, even when the transported substrate is light transmissive or non-transmissive, the micro inspection unit 106 can inspect the minute defect of any substrate by properly using the illumination systems. That is, the micro inspection unit 106 makes it possible to perform the both types of defect inspection of the light transmissive substrate and the light non-transmissive substrate in spite of the simple structure by using the two illumination systems and the micro cameras commonly used therefor, in the same manner as the macro inspection unit 104. A marker 132 for marking the defect portion of the substrate P detected by the micro inspection unit 106 and a driving system 132a therefor are provided between the transmitting light illumination for macro 114 and the transmitting light illumination for micro 124 under or below the transport system 108. An ink jet head or a magic ink can be used for the marker 132.

<Inspection Step (Inspection Method Based on Use of Inspection Apparatus)>

Next, an explanation will be made about the operation of the inspection apparatus 102 and an example of the substrate inspection method.

A. Inspection of Light Non-Transmissive Substrate

Figure 4:
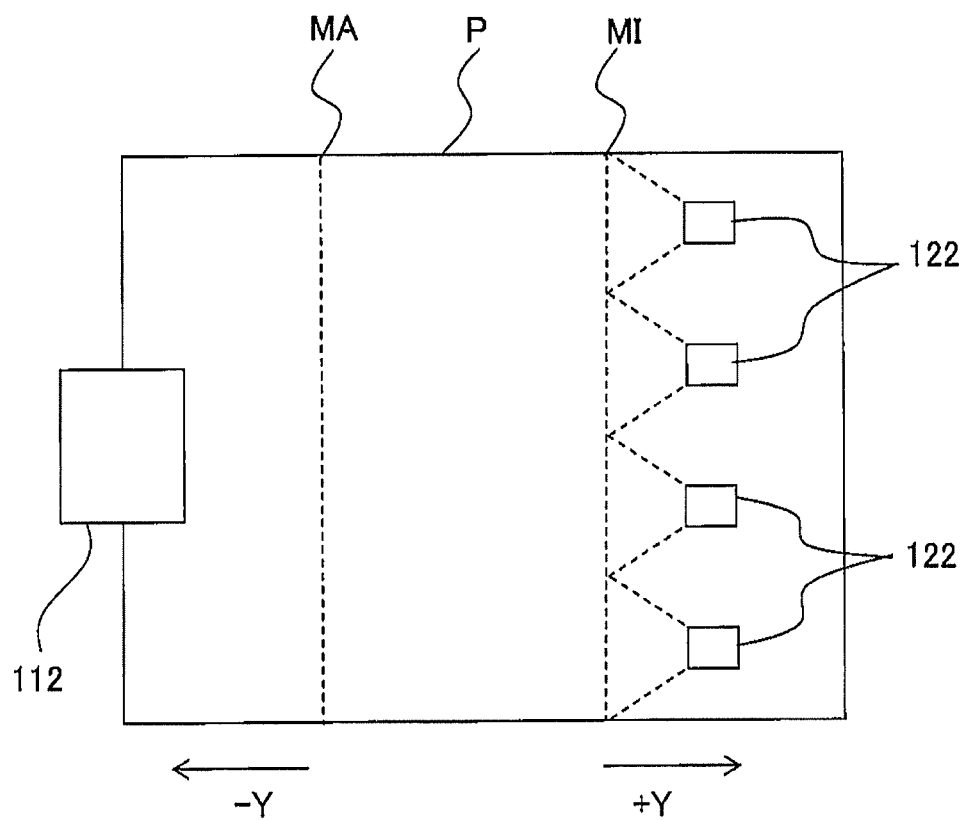
FIG. 4 shows an arrangement of a substrate as an inspection objective, a macro camera, and micro cameras as viewed from a position over or above the inspection apparatus.

FIG. 4 shows an arrangement of the light non-transmissive substrate P as an inspection objective, the macro camera 112, and the micro cameras 122 as viewed from a position over or above the inspection apparatus 102. In this embodiment, when the substrate P is inspected, the minute defect is firstly inspected by means of the micro inspection unit 106. The control unit 111 turns ON the non-transmitting light illumination for micro 126 (see FIG. 2A), and the control unit 111 controls the transport system 108 so that the substrate P is transported in the +Y direction toward the micro detection position MI. When the substrate P passes over the micro detection position MI on the travel route, the scattered light coming from the surface of the substrate P is received by the four micro cameras 122. The intensity of the received light is inputted into the control system 111 together with the coordinate position in the transport direction of the substrate P. The control system 111 is provided with an image processing unit 111a in which the light intensities received from the micro detection position MI by the four micro cameras 122 are allowed to correspond in relation to each of the coordinate positions on the substrate P (X coordinate position and Y coordinate position). Thus, the micro inspection image, which represents the light intensity of the entire substrate P, is synthesized by the image processing unit 111a on the basis of the light intensity in relation to each of the coordinate positions. The pixel positions of the micro cameras 122 are previously allowed to correspond to the positions of the substrate P in the transport direction (Y direction) and the X direction perpendicular thereto.

When the micro inspection is completed as described above, then the control system 111 subsequently turns OFF the non-transmitting light illumination for micro 126, and the control system 111 turns ON the non-transmitting light illumination for macro 116 in place thereof. Further, the control system 111 controls the transport system 108 so that the substrate P is moved in the direction (−Y direction) opposite to the transport direction, i.e., on the travel return route of the movement route of the micro inspection. When the substrate P passes over the macro detection position MA on the travel route, the scattered light coming from the surface of the substrate P is received by the macro camera 112. As described above, the resolution of the macro camera 112 is lower than the resolution of the micro camera. However, the field of the macro camera 112 is wide, and hence the scattered light can be detected over the entire region in the X direction of the substrate by using one camera. The intensity of the received light is inputted into the control system 111 together with the coordinate position of the substrate P in the transport direction. In the image processing unit 111a of the control system 111, the light intensity received from the macro inspection position MA by the macro camera 112 is allowed to correspond in relation to each of the coordinate positions on the substrate P (positions in the transport direction (Y direction) and positions in the direction (X direction) perpendicular thereto). Thus, the macro inspection image, which represents the intensity of the light of the entire substrate P, is synthesized by the image processing unit 111a on the basis of the light intensity in relation to each of the position coordinates.

B. Inspection of Light Transmissive Substrate

Figure 5A:
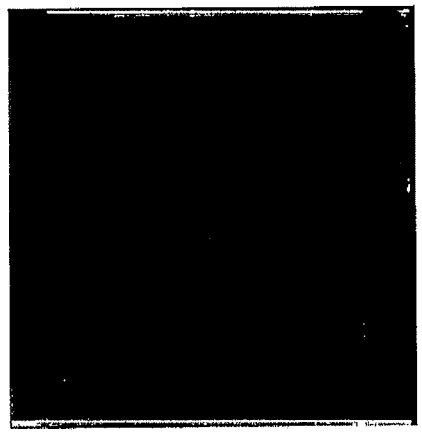
FIG. 5A shows a micro inspection image obtained from a substrate having a concave-convex pattern formed by using a sol-gel material on a glass substrate.

When the substrate as the inspection objective is the light transmissive substrate, then the transmitting light illumination for micro 124 is used in place of the non-transmitting light illumination for micro 126, and the transmitting light illumination for macro 114 is used in place of the non-transmitting light illumination for macro 116. In the inspection operation, the minute defect is firstly inspected by means of the micro inspection unit 106, while moving the substrate P in the transport direction in the same manner as the case shown in FIG. 4. That is, the control system 111 turns ON the transmitting light illumination for micro 124 (see FIG. 2A), and the control system 111 controls the transport system 108 so that the substrate P is transported in the +Y direction toward the micro detection position MI. When the substrate P passes over the micro detection position MI, the scattered light coming from the surface of the substrate P is received by the four micro cameras 122. The intensity of the received light is inputted into the control system 111 together with the coordinate position in the transport direction of the substrate P. In the image processing unit 111a of the control system 111, the light intensities received from the micro detection position MI by the four micro cameras 122 are allowed to correspond in relation to each of the coordinate positions on the substrate P (X coordinate position and Y coordinate position). Thus, the micro inspection image, which represents the light intensity of the entire substrate P, is synthesized by the image processing unit 111a on the basis of the light intensity in relation to each of the coordinate positions. FIG. 5A shows an example of the synthesized micro inspection image. FIG. 5A shows the micro inspection image obtained from a substrate having a concave-convex pattern formed by using a sol-gel material on a glass substrate as described later on.

Figure 5B:
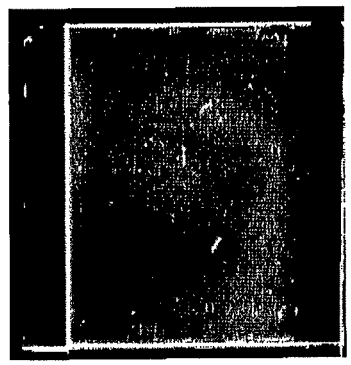
FIG. 5B shows a macro inspection image obtained from a substrate having a concave-convex pattern formed by using a sol-gel material on a glass substrate.

When the micro inspection is completed, then the control system 111 subsequently turns OFF the non-transmitting light illumination for micro 126, and the control system 111 turns ON the transmitting light illumination for macro 114 in place thereof. Further, the control system 111 controls the transport system 108 so that the substrate P is moved on the travel return route (−Y direction) of the movement route of the micro inspection. When the substrate P passes over the macro detection position MA, the scattered light coming from the surface of the substrate P is received by the macro camera 112. The intensity of the received light is inputted into the control system 111 together with the coordinate position of the substrate P in the transport direction. In the control system 111, the light intensity received from the macro inspection position MA by the macro camera 112 is allowed to correspond in relation to each of the coordinate positions on the substrate P. Thus, the macro inspection image, which represents the intensity of the light of the entire substrate P, is synthesized by the image processing unit 11a of the control system 111 on the basis of the light intensity of each of the position coordinates. FIG. 5B shows an example of the synthesized macro inspection image. FIG. 5B shows the macro inspection image obtained from a substrate having a concave-convex pattern formed by using a sol-gel material on a glass substrate as described later on.
<Judging Step>

The luminance of each of the pixels of the micro inspection image synthesized by the image processing unit 111a in the inspection step described above is evaluated by the control system 111. If any part or portion, in which the luminance is higher or lower than a certain luminance, is present and the size of the part or portion is not less than a predetermined size, then the concerning part or portion is judged as the defect, and the coordinate of the defect and the image therearound are stored in a storage unit 111b of the control system 111. Further, the coordinate, on which the defect exists, is fed to the marker 132. The transport system 108 and the marker driving system 132a are driven to move the marker 132 while confronting the defect portion of the substrate P. A mark is affixed to the defect portion by the marker 132 from the back surface of the substrate (marking step). It is not necessarily indispensable to perform the marking step. However, the marking step is useful, for example, in order to specify the position of the defect portion, for example, when the defect position is analyzed. Further, the luminance of each of the pixels of the macro inspection image synthesized by the image processing unit 111a in the inspection step described above is evaluated by the control system 111. If the portion, in which the luminance is higher or lower than a certain luminance, has the areal size which is smaller than a certain areal size, it is judged that the product is a non-defective (satisfactory) product. If the portion has the areal size which is larger than the certain areal size, it is judged that the product is a defective product.
<Aftertreatment Step>

If it is judged in the judging step that the luminance unevenness and the defect are within the desired ranges, the organic EL element is produced in accordance with the process described later on by using the substrate. If it is judged that the luminance unevenness or the defect is without the desired range, the aftertreatment is applied. In the aftertreatment, it is analyzed whether the defect (luminance unevenness) of the substrate is caused by the dust, the scratch, the periodic error, or the random error. If the defect is caused by any adhered matter such as the dust or the like, the repair can be performed, for example, by blowing off the adhered matter by applying the pressurized air to the substrate surface. After that, the inspection as described above is performed again. If the inspection as described above is performed for a plurality of substrates in accordance with the continuous system or the batch system, it is possible to provide such a step that those in which the ratio of the maximum value with respect to the minimum value, the scattering intensity difference, or the average pixel value is within the desired range are distinguished from those in which the ratio of the maximum value with respect to the minimum value, the scattering intensity difference, or the average pixel value is without the range, on the basis of the inspection result. Those in which the ratio of the maximum value with respect to the minimum value, the scattering intensity difference, or the average pixel value is within the range can be supplied, for example, to a production line for the organic EL element or the like to successively produce the organic EL element. Those in which the ratio of the maximum value with respect to the minimum value, the scattering intensity difference, or the average pixel value is without the range can be subjected to the defect analysis or can be discarded all at once.
<Substrate Manufacturing Step>

An explanation will be made below about the step of manufacturing (preparing) the substrate used for the inspection apparatus of the present invention and the inspection method based on the use of the same. The inspection apparatus of the present invention and the inspection method based on the use of the same are advantageous, for example, for the process for producing the light transmissive substrate having the concave-convex pattern when the step of manufacturing a light non-transmissive mold or replica for producing such a light transmissive substrate in accordance with the transfer process is present. That is, as described above, in the inspection apparatus and the inspection method of the present invention, the illumination system can be switched depending on the light transmission characteristic of the substrate as the inspection objective to inspect the luminance unevenness and the pattern defect. Therefore, it is possible to employ, as the inspection objective, not only the light transmissive substrate having the concave-convex pattern provided as the product but also any one of the concave-convex patterns of the light non-transmissive mold and the replica for producing the same. An explanation will be made below as exemplified by the production process for procuring the light transmissive substrate used for the light scattering substrate of the organic EL by way of example.

In order to produce the substrate having the irregular concave-convex surface, it is preferable to use a method in which the self-organization or self-assembly (micro phase separation) of block copolymer is utilized as described in Japanese Patent Application No. 2011-006487 (WO2012/096368A1) filed by the present applicant (hereinafter referred to as "BCP (Block Copolymer) method" as appropriate) and a method in which concavities and convexities are formed by using wrinkles on the polymer surface by heating and cooling a polymer film on a vapor-deposited film as disclosed in PCT/JP2010/062110 (WO2011/007878A1) filed by the present applicant (hereinafter referred to as "BKL (Buckling) method" as appropriate) as explained below. The respective methods will be explained.

A. Production of Substrate by BCP Method

An explanation will be made with reference to FIGS. 6 to 9 about the production of the substrate by means of the BCP method.

[Preparation Step of Block Copolymer Solution]

The block copolymer used for the BCP method includes at least a first polymer segment composed of a first homopolymer and a second polymer segment composed of a second homopolymer different from the first homopolymer. The second homopolymer desirably has a solubility parameter which is higher than a solubility parameter of the first homopolymer by 0.1 $(cal/cm^3)^{1/2}$ to 10 $(cal/cm^3)^{1/2}$. In a case that the difference in the solubility parameter between the first and second homopolymers is less than 0.1 $(cal/cm^3)^{1/2}$, it is difficult to form a regular micro phase separation structure of the block copolymer. In a case that the difference exceeds 10 $(cal/cm^3)^{1/2}$, it is difficult to prepare a uniform or homogeneous solution of the block copolymer.

Examples of monomers serving as raw materials of homopolymers usable as the first homopolymer and the second homopolymer include styrene, methylstyrene, propylstyrene, butylstyrene, hexylstyrene, octylstyrene, methoxystyrene, ethylene, propylene, butene, hexene, acrylonitrile, acrylamide, methyl methacrylate, ethyl methacrylate, propyl methacrylate, butyl methacrylate, hexyl methacrylate, octyl methacrylate, methyl acrylate, ethyl acrylate, propyl acrylate, butyl acrylate, hexyl acrylate, octyl acrylate, methacrylic acid, acrylic acid, hydroxyethyl methacrylate, hydroxyethyl acrylate, ethylene oxide, propylene oxide, dimethylsiloxane, lactic acid, vinylpyridine, hydroxystyrene, styrenesulfonate, isoprene, butadiene, ε-caprolactone, isopropylacrylamide, vinyl chloride, ethylene terephthalate, tetrafluoroethylene, and vinyl alcohol. Among these monomers, styrene, methyl methacrylate, ethylene oxide, butadiene, isoprene, vinylpyridine, and lactic acid are preferably used from the viewpoints that the formation of phase separation easily occurs, and that concavities and convexities are easily formed by means of the etching.

Further, examples of a combination of the first homopolymer and the second homopolymer may include combinations of two selected from the group consisting of a styrene-based polymer (more preferably, polystyrene), polyalkyl methacrylate (more preferably, polymethyl methacrylate), polyethylene oxide, polybutadiene, polyisoprene, polyvinylpyridine, and polylactic acid. Among these combinations, a combination of the styrene-based polymer and polyalkyl methacrylate, a combination of the styrene-based polymer and polyethylene oxide, a combination of the styrene-based polymer and polyisoprene, and a combination of the styrene-based polymer and polybutadiene are more preferable, and the combination of the styrene-based polymer and polymethyl methacrylate, the combination of the styrene-based polymer and polyisoprene, and the combination of the styrene-based polymer and polybutadiene are particularly preferable, from the viewpoints that the depth of the concavities and convexities formed in the block copolymer can be further deepened by preferentially removing one homopolymer by means of the etching process. A combination of polystyrene (PS) and polymethyl methacrylate (PMMA) is more preferred.

The number average molecular weight (Mn) of the block copolymer is preferably not less than 500,000, and more preferably not less than 1,000,000, and particularly preferably in a range of 1,000,000 to 5,000,000. In a case that the number average molecular weight is less than 500,000, the average pitch of the concavities and convexities formed by the micro phase separation structure of the block copolymer is so small that the average pitch of the concavities and convexities of the obtained diffraction grating becomes insufficient. Especially, in a case of the diffraction grating used for the organic EL, it is necessary to diffract the illumination light over a range of wavelength of the visible region, and thus the average pitch is desirably in a range of 100 nm to 1,500 nm. In view of this point, the number average molecular weight (Mn) of the block copolymer is preferably not less than 500,000. On the other hand, according to an experiment performed by the present applicant, as described later on, the following fact has been revealed. That is, when the number average molecular weight (Mn) of the block copolymer is not less than 500,000, if the second heating step is not performed after the etching step, then it is difficult to obtain any desired concave-convex pattern by means of the electroforming.

The molecular weight distribution (Mw/Mn) of the block copolymer is preferably not more than 1.5, and is more preferably in a range of 1.0 to 1.35. In a case that the molecular weight distribution as described above exceeds 1.5, it is not easy to form the regular micro phase separation structure of the block copolymer.

Note that the number average molecular weight (Mn) and the weight average molecular weight (Mw) of the block copolymer are values measured by the gel permeation chromatography (GPC) and converted to the molecular weights of standard polystyrene.

In the block copolymer, the volume ratio between the first polymer segment and the second polymer segment (the first polymer segment: the second polymer segment) is desirably in a range of 3:7 to 7:3 and more preferably 4:6 to 6:4 in order to generate a lamella structure by the self-organization or self-assembly. In a case that the volume ratio is out of the range described above, it is difficult to form a concave-convex pattern (concavity and convexity pattern) resulting from the lamella structure.

The block copolymer solution used for the BCP method is prepared by dissolving the block copolymer in a solvent. Examples of the solvent include aliphatic hydrocarbons such as hexane, heptane, octane, decane, and cyclohexane; aromatic hydrocarbons such as benzene, toluene, xylene, and mesitylene; ethers such as diethyl ether, tetrahydrofuran, and dioxane; ketones such as acetone, methyl ethyl ketone, isophorone, and cyclohexanone; ether alcohols such as butoxyethyl ether, hexyloxyethyl alcohol, methoxy-2-propanol, and benzyloxyethanol; glycol ethers such as ethylene glycol dimethyl ether, diethylene glycol dimethyl ether, triglyme, propylene glycol monomethyl ether, and propylene glycol monomethyl ether acetate; esters such as ethyl acetate, ethyl lactate, and γ-butyrolactone; phenols such as phenol and chlorophenol; amides such as N,N-dimethylformamide, N,N-dimethylacetamide, and N-methylpyrrolidone; halogen-containing solvents such as chloroform, methylene chloride, tetrachloroethane, monochlorobenzene, and dichlorobenzene; hetero-element containing compounds such as carbon disulfide; and mixture solvents thereof. The percentage content of the block copolymer in the block copolymer solution is preferably in a range of 0.1% by mass to 15% by mass, and more preferably in a range of 0.3% by mass to 5% by mass, relative to 100% by mass of the block copolymer solution.

In addition, the block copolymer solution may further contain, for example, another homopolymer (a homopolymer other than the first homopolymer and the second homopolymer in the block copolymer contained in the solution: for example, in a case that the combination of the first homopolymer and the second homopolymer in the block copolymer is the combination of polystyrene and polymethyl methacrylate, the another homopolymer may be any kind of homopolymer other than polystyrene and polymethyl methacrylate), a surfactant, an ionic compound, an antifoaming agent, and a leveling agent.

When the another homopolymer is contained, it is thereby possible to improve the micro phase separation structure of the block copolymer. For example, it is possible to use polyalkylene oxide in order to further deepen the depth of the concavities and convexities formed by the micro phase separation structure. As the polyalkylene oxide as described above, polyethylene oxide or polypropylene oxide is more preferred, and polyethylene oxide is particularly preferred. Further, as the polyethylene oxide as described above, one represented by the following formula is preferred:

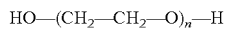

HO—(CH$_2$—CH$_2$—O)$_n$—H

[in the formula, "n" represents an integer in a range of 10 to 5,000 (more preferably an integer in a range of 50 to 1,000, and further preferably an integer in a range of 50 to 500)].

If the value of n as described above is less than the lower limit described above, then the molecular weight is too low, and the substance is lost, for example, by the volatilization and/or the evaporation on account of the heating process at a high temperature, and the effect obtained by containing the another homopolymer is scarce. If the value of n exceeds the upper limit, then the molecular weight is too high, and the molecular motility is low. Therefore, the velocity of phase separation is slowed down, and any harmful influence is exerted on the formation of the micro phase separation structure.

Further, the number average molecular weight (Mn) of the another homopolymer as described above is preferably in a range of 460 to 220,000, and is more preferably in a range of 2,200 to 46,000. If the number average molecular weight is less than the lower limit, then the molecular weight is too low, the substance is lost, for example, by the volatilization and/or the evaporation on account of the heating process at a high temperature, and the effect obtained by containing the another homopolymer is scarce. If the number average molecular weight exceeds the upper limit, then the molecular weight is too high, and the molecular motility is low. Therefore, the velocity of phase separation is slowed down, and any harmful influence is exerted on the formation of the micro phase separation structure.

The molecular weight distribution (Mw/Mn) of the another homopolymer as described above is preferably not more than 1.5, and more preferably in a range of 1.0 to 1.3. In a case that the molecular weight distribution exceeds the upper limit, it is difficult to maintain the uniformity of shape of the micro phase separation. Note that the number average molecular weight (Mn) and the weight average molecular weight (Mw) as described above are values measured by the gel permeation chromatography (GPC) and converted to molecular weights of standard polystyrene.

Further, when the another homopolymer is used in the BCP method, it is preferable that the combination of the first homopolymer and the second homopolymer in the block copolymer is the combination of polystyrene and polymethyl methacrylate (polystyrene-polymethyl methacrylate), and the another homopolymer is polyalkylene oxide. By using a polystyrene-polymethyl methacrylate block copolymer and polyalkylene oxide in combination as described above, the orientation in the vertical direction is further improved, thereby making it possible to further increase the depths of the concavities and convexities on the surface, and to shorten the heating process time or the solvent annealing process time described later on during the production.

When the another homopolymer is contained in the block copolymer solution described above, the total percentage content of the block copolymer and the another homopolymer is preferably in a range of 0.1% by mass to 15% by mass, and more preferably in a range of 0.3% by mass to 5% by mass, in the block copolymer solution. In a case that the total percentage content is less than the lower limit, it is not easy to uniformly apply the solution on a base member (coat a base member with the solution) in order to attain a film of which thickness is sufficient to obtain a necessary film thickness. In a case that the total percentage content exceeds the upper limit, it is relatively difficult to prepare a solution in which the block copolymer and the another homopolymer are uniformly dissolved in the solvent.

When the another homopolymer is used, it is preferable that the content is not more than 100 parts by mass with respect to 100 parts by mass of the block copolymer. It is more preferable that the content is in a range of 5 parts by mass to 100 parts by mass. If the content of the another homopolymer as described above is less than the lower limit, the effect obtained by containing the another homopolymer is scarce. When polyalkylene oxide is used as the another homopolymer, the content thereof is more preferably in a range of 5 parts by mass to 70 parts by mass. If the content of polyalkylene oxide exceeds 100 parts by mass with respect to 100 parts by mass of the block copolymer, the concave-convex pattern, which is formed by the phase separation of the block copolymer, collapses with ease. On the other hand, if the content of polyalkylene oxide exceeds 70 parts by mass, polyalkylene oxide is deposited in some cases.

In a case that the surfactant is used, the content of the surfactant is preferably not more than 10 parts by mass, relative to 100 parts by mass of the block copolymer. Further, in a case that the ionic compound is used, the content of the ionic compound is preferably not more than 10 parts by mass, relative to 100 parts by mass of the block copolymer.

[Block Copolymer Solution Coating Step]

Figure 6A:
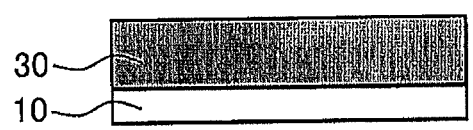
FIGS. 6A to 6D conceptually show the process for manufacturing the substrate by the BCP method, conceptually illustrating the process to obtain a mountain-like structure by performing a first heating step, an etching step, and a second heating step.

According to the substrate production method based on the use of the BCP method, as shown in FIG. 6A, the block copolymer solution prepared as described above is applied onto a base member 10 (a base member 10 is coated with the block copolymer solution) to form a thin film 30. The base member 10 is not especially limited. However, the base member 10 includes, for example, resin substrates of resins such as polyimide, polyphenylene sulfide (PPS), polyphenylene oxide, polyether ketone, polyethylene naphthalate, polyethylene terephthalate, polyarylate, triacetyl cellulose, and polycycloolefin; inorganic substrates such as glass, octadecyldimethyl chlorosilane (ODS) treated glass, octadecyl trichlorosilane (OTS) treated glass, organo silicate treated glass, glass substrates treated with a silane coupling agent, and silicon substrates; and metal substrates of metals such as aluminum, iron, and copper. Further, the base member 10 may be subjected to a surface treatment such as an orientation treatment, etc. For example, the organo silicate treated glass can be prepared by coating a glass with a methyl isobutyl ketone (MIBK) solution of methyl trimethoxysilane (MTMS) and 1,2-bis(trimethoxysilyl) ethane (BTMSE), and then performing the heating process therefor. Each of the octadecyldimethyl chlorosilane treated glass and octadecyl trichlorosilane treated glass can be prepared by such a method including immersing a glass in a heptane solution of one of octadecyldimethyl chlorosilane and octadecyl trichlorosilane beforehand, and washing out the unreacted portion from the glass thereafter. In such a manner, it is allowable to perform the surface treatment for a surface of the substrate such as the glass with a primer layer of octadecyldimethyl chlorosilane, organo silicate, etc., or to perform the silane coupling treatment for the substrate surface with a general silane coupling agent, thereby making it possible to improve the adhesion property of the block copolymer to the substrate. In a case that the adhesion property is not sufficient, the block copolymer drops off or detaches (peels off or exfoliates) from the substrate during the electroforming, which in turn adversely affects the production of a mold for transferring. Note that when the surface of the substrate such as glass or the like is treated with ODS, organosilicate or the like, then the micro phase separation structure, which includes, for example, the lamella structure, the cylinder structure, and the spherical structure, is easily arranged perpendicularly with respect to the surface in the heating step described later on, for the following reason. That is, the interface energy different is decreased between the block copolymer component and the substrate surface, and thus the domains of the respective blocks for constructing the block copolymer are easily oriented perpendicularly.

The method for applying the block copolymer solution onto the base member (coating the base member with the block copolymer) is not particularly limited, for which it is allowable to employ, for example, the spin coating method, spray coating method, dip coating method, dropping method, gravure printing method, screen printing method, relief printing method, die coating method, curtain coating method, and ink-jet method.

As for the thickness of the thin film 30 of the block copolymer, as will be described later on, the thickness of a coating film after being dried is preferably in a range of 10 nm to 3,000 nm, and more preferably in a range of 50 nm to 500 nm.
[Drying Step]

After the base member 10 is coated with the block copolymer solution to form the thin film 30, the thin film 30 on the base member 10 is dried. The drying can be performed in an atmosphere of the atmospheric air. The temperature for drying the thin film 30 is not particularly limited, provided that the solvent can be removed from the thin film 30. For example, the drying temperature is preferably in a range of 10° C. to 200° C., and more preferably in a range of 20° C. to 100° C. Note that the drying step starts the formation of micro phase separation structure of the block copolymer, which results in appearance of concavities and convexities on the surface of the thin film 30 in some cases.
[First Heating Step]

Figure 6B:
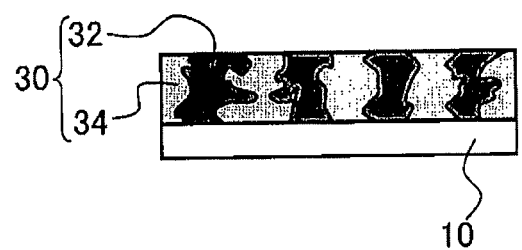

After the drying step, the thin film 30 is heated at a temperature of not less than the glass transition temperature (Tg) of the block copolymer (first heating step or annealing step). The heating step (example of the step of generating the micro phase separation structure) allows the self-organization or self-assembly of the block copolymer to proceed. As shown in FIG. 6B, the block copolymer is subjected to the micro phase separation into portions of a first polymer segment 32 and a second polymer segment 34. If the heating temperature is less than the glass transition temperature of the block copolymer, then the molecular motility of the polymer is low, and the self-organization or self-assembly of the block copolymer does not proceed sufficiently. The micro phase separation structure cannot be formed sufficiently, or the heating time, which is required to sufficiently generate the micro phase separation structure, is prolonged. Further, the upper limit of the heating temperature is not specifically limited, provided that the heating temperature is a temperature at which the block copolymer is not thermally decomposed. The first heating step can be performed in the atmosphere of the atmospheric air by using, for example, an oven. Note that the heating temperature may be gradually raised to continuously perform the drying step and the heating step. By doing so, the drying step is included in the heating step.
[Etching Step]

Figure 6C:
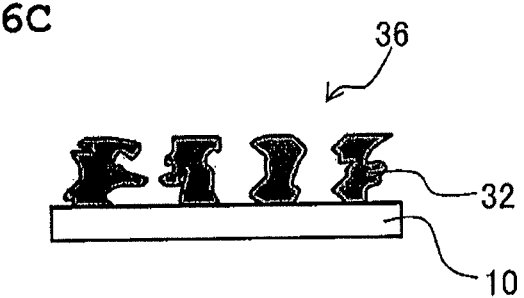

The etching process is performed for the thin film 30 after the first heating step. The molecular structure of the first polymer segment 32 is different from that of the second polymer segment 34. Therefore, the easiness of etching also differs therebetween. Therefore, it is possible to selectively remove the polymer segment, i.e., one polymer segment (second polymer segment 34) for constructing the block copolymer, by means of the etching process depending on the type of the homopolymer. As shown in FIG. 6C, the second polymer segment 34 is removed from the micro phase separation structure by means of the etching process, and the conspicuous concave-convex structure appears in the coating film. Those adoptable for the etching process described above include, for example, the reactive ion etching method, the ozone oxidization method, the hydrolysis method, the metal ion dyeing (staining) method, and the ultraviolet etching method. Further, as for the etching process, it is also allowable to adopt a method in which the covalent bond of the block copolymer is treated with at least one selected from the group consisting of acids, bases, and reducing agents to cut or cleave the covalent bond, and then the coating film formed with the micro phase separation structure is cleaned or washed, for example, with a solvent for dissolving only one polymer segment so that only the one polymer segment is removed thereby while maintaining the micro phase separation structure. In the embodiment described later on, the ultraviolet etching is used, for example, in view of the easiness of the operation.
[Second Heating Step]

The second heating or annealing process is applied to the concave-convex structure 36 of the thin film 30 obtained by the etching step described above. The heating temperature in the second heating process is desirably not less than the glass transition temperature of the first polymer segment 32 allowed to remain after the etching, i.e., not less than the glass transition temperature of the first homopolymer. For example, the heating temperature is desirably not less than the glass transition temperature of the first homopolymer and not more than a temperature which is higher than the glass transition temperature of the first homopolymer by 70° C. If the heating temperature is less than the glass transition temperature of the first homopolymer, then the desired concave-convex structure, i.e., the smooth mountain-like structure is not obtained after the electroforming, or a long time is required for the heating. If the heating temperature is considerably higher the glass transition temperature of the first homopolymer, then the first polymer segment 32 is melted, and/or the shape collapses greatly, which is not preferred. In view of the above, it is desirable that the heating is performed within a range from the glass transition temperature to the temperature higher than the glass transition temperature by about 70° C. The second heating process can be also performed in the atmosphere of the atmospheric air by using, for example, an oven, in the same manner as the first heating process.

According to an experiment performed by the present inventors, the following fact has been revealed. That is, any desired transfer pattern is hardly obtained, although the concave-convex structure is transferred to a metal mold by means of the electroforming as described later on by using, as a master (master block or mold), the concave-convex structure 36 of the coating film obtained by the etching step. In particular, this problem is more conspicuous when the molecular weight of the block copolymer is larger. As described above, the molecular weight of the block copolymer deeply relates to the micro phase separation structure, and consequently the pitch of the diffraction grating obtained therefrom. Therefore, when the diffraction grating is used for the way of use of the organic EL element or the like, it is necessary to provide the pitch distribution so that the diffraction is caused in the wavelength region which is wide or extensive like the visible region and which includes the wavelength band having relatively long wavelengths. In order to realize such a situation, it is necessary to reliably obtain the concave-convex structure having the desired pitch distribution as described above by means of the electroforming, even in the case of the use of the block copolymer having a relatively high molecular weight. In the present invention, the concave-convex structure, which is obtained by the etching, is subjected to the heating process. Thus, the metal substrate (mold), in which the concave-convex structure is sufficiently reflected, can be obtained even in the case of the electroforming step performed thereafter.

The reason thereof is considered as follows by the present inventors. The concave-convex structure 36 after the etching is considered to have a complicated cross-sectional structure in which the grooves defined by the concave-convex structure have rough side surfaces and the concavities and convexities (including overhangs) are generated in the direction perpendicular to the thickness direction. The following three problems arise on account of the complicated cross-sectional structure as described above.

i) The portion, to which the seed layer for the electroforming does not adhere, is generated in the complicated cross-sectional structure, and it becomes difficult to uniformly accumulate the metal layer by means of the electroforming. As a result, an obtained metal substrate has a low mechanical strength, which causes the occurrence of any defect including, for example, the deformation of the metal substrate and the pattern deficiency.

ii) In the case of the electroforming (electroplating), the thickness of plating of each portion differs depending on the shape of the object subjected to the plating. In particular, the plating metal is easily attracted by the convexity (protrusion) and the projecting corner of the object, and the plating metal is hardly attracted by the concavity (recess) and the recessed (dented) portion. Also from the reason as described above, the cross-sectional structure having the complicated concavities and convexities after the etching makes it difficult to obtain an electroforming film having a uniform film thickness.

iii) Even when the complicated cross-sectional structure as described above can be transferred to the metal substrate by means of the electroforming, if it is intended to transfer the concave-convex shape by pressing the metal substrate against a curable resin, then the curable resin enters the gaps of the complicated cross-sectional structure of the metal substrate, and hence the metal substrate cannot be exfoliated (released or peeled off) from the resin after the curing, or any portion of the metal substrate having a weak strength is broken to cause the pattern deficiency. Note that in the conventional technique, in order to solve this problem, the transfer is repeatedly performed with polydimethylsiloxane (PDMS).

In the BCP method, the concave-convex structure after the etching is heated, and thus the first polymer segment 32 for constructing the side surface of the groove is subjected to the annealing process. As conceptually shown in FIG. 6D, the cross-sectional shape defined by the first polymer segment 32 is formed into a mountain-like shape which is composed of relatively smooth inclined surfaces and which is tapered upwardly from the base member (referred to as "mountain-like structure" in this patent application). In the case of the mountain-like structure as described above, no overhang appears. The metal layer, which is accumulated in the first polymer segment 32, is replicated or duplicated into a reversed pattern (inverted pattern) thereof. Therefore, the exfoliation is performed with ease. It has been clarified that the three problems described above can be solved in accordance with the action of the second heating step as described above. The present applicant has revealed the following fact. That is, when a photograph of scanning electron microscope (SEM) is taken to show a cross-sectional structure of a metal substrate formed by the Ni electroforming from a concave-convex structure obtained by performing the heating process after the etching process for the block copolymer, then the concavities and convexities are smooth, the convexities provide gentle mountain-like shapes, and any overhang is not observed at all. On the other hand, in the case of an SEM photograph to show a cross-sectional structure of a metal substrate formed by the Ni (nickel) electroforming from a concave-convex structure obtained without performing the second heating process after the etching process for the block copolymer, the following situation has been confirmed. That is, the Ni portion forms grooves having complicated shapes including overhang structures, and the resin enters the inside thereof.

The mountain-like structure 38 is formed by performing the first heating step, the etching step, and the second heating step as described above. However, in place thereof, it is also allowable to form a wave-like structure in accordance with the solvent annealing step explained below. In this case, in the preparation step for the block copolymer solution described above, the volume ratio between the first polymer segment and the second polymer segment in the block copolymer (first polymer segment: second polymer segment) is preferably within a range of 4:6 to 6:4 and more preferably about 5:5 in order to generate the horizontal cylinder structure by means of the self-organization or self-assembly as described later on. If the volume ratio is without the range as described above, then it is difficult to form the concave-convex pattern resulting from the horizontal cylinder structure, and there is such a tendency that a spherical or vertical cylinder structure appears.

[Solvent Annealing Step]

Figure 7A:
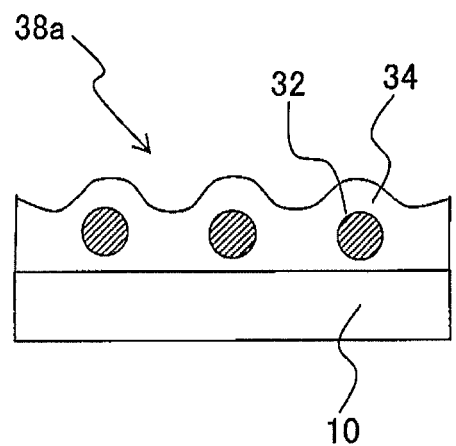
FIG. 7A conceptually shows the process to obtain wave-like structures by the BCP method while performing a solvent annealing step and shows a wave-like structure in which the cylindrical arrangement includes a single layer.

After the drying step described above, the thin film 30 is subjected to the solvent annealing process (solvent phase-separation process) under an atmosphere of the vapor of an organic solvent so that a phase separation structure of the block copolymer is formed inside the thin film 30. With this solvent annealing process, the self-organization of the block copolymer is advanced, and the block copolymer undergoes the micro phase separation into a portion corresponding to a first polymer segment 32 and a portion corresponding to a second polymer segment 34 as shown in FIG. 7A.

For example, the solvent annealing process can be carried out by providing an atmosphere of the vapor of organic solvent (organic solvent vapor) inside a tightly sealable container such as a desiccator, and exposing the thin film 30 as the objective under this atmosphere. The organic solvent to be used in the solvent annealing process is preferably an organic solvent of which boiling point is in a range of 20° C. to 120° C. It is possible to use, for example, chloroform, dichloromethane, toluene, tetrahydrofuran (THF), acetone, carbon disulfide, and mixture solvents thereof. Among these solvents, it is preferable to use chloroform, dichloromethane, acetone, a mixture solvent of acetone/carbon disulfide.

The concentration of the organic solvent vapor is preferably high for the purpose of promoting the phase separation of the block copolymer, which is desirably saturated vapor pressure, wherein the concentration is controlled or managed relatively easily as well. For example, in a case that the organic solvent is chloroform, the saturated vapor amount (quantity) is known to be in a range of 0.4 g/l to 2.5 g/l at room temperature (0° C. to 45° C.). As for the atmosphere temperature of the solvent annealing, it is appropriate that the process is performed at 0° C. to 45° C. If the temperature is higher than 45° C., then the concave-convex structure formed on the thin film is blunt or dull (loosened), and the concave-convex structure collapses with ease. In an environment lower than 0° C., then the organic solvent is hardly evaporated, and the phase separation of the block copolymer hardly occurs. The treatment time of the solvent annealing process may be 6 hours to 168 hours, preferably 12 hours to 48 hours, and more preferably 12 hours to 36 hours. If the time of the solvent annealing process is excessively long, there is such a tendency that the another homopolymer is deposited on the surface of the applied film (coating film) and/or the concave-convex shape is collapsed (loosened). On the other hand, if the time of the annealing process is excessively short, then the grooves of the concave-convex structure are shallow, and the diffraction effect is insufficient when the diffraction grating is manufactured by using the mold.

Normally, the following is known as a general rule. In a case that the mixing ratio between the first homopolymer and the second homopolymer for constructing the block copolymer is even (5:5) or approximately even, a phase separation structure of the lamella type appears by the thermal annealing process. In a case that the mixing ratio is approximately 3:7, a cylinder structure appears. In a case that the mixing ratio is approximately 2:8, a spherical structure appears. However, the present applicant has found out that when the solvent annealing process is performed, then the phase separation occurs while generating a cylinder structure in the horizontal direction even in a case that the mixing ratio of the first homopolymer and the second homopolymer for constructing the block copolymer is in a range of 4:6 to 6:4. Although the reason for the above phenomenon is not clear, the present applicant considers as follows. That is, the organic solvent permeates into one of the homopolymers to cause one of the homopolymers to swell. As a result, the apparent volume ratio between the first homopolymer and the second homopolymer is different from the actual mixing ratio between the first homopolymer and the second homopolymer.

Figure 7B:
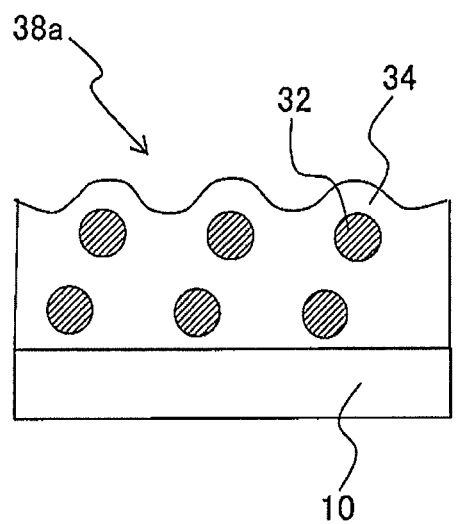
FIG. 7B shows conceptually shows the process to obtain wave-like structures by the BCP method while performing a solvent annealing step a wave-like structure in which the cylindrical structure includes a plurality of layers.

In the horizontal cylinder structure, a first homopolymer 32 is present in a layer of a second homopolymer 34, and the first homopolymer 32 is oriented in a form of cylinders to extend in a direction substantially parallel to the surface of the base member 10, as shown in FIG. 7A. As a result, a surface (top) layer portion of the second homopolymer 34 is smoothly raised or bulged to form a wave-like shape, at portions at which the first homopolymer 32 is present. Note that it is allowable that the cylinder-like arrangement, in which the first homopolymer 32 extends in the direction substantially parallel to the surface of the base member 10, is formed in a plurality of layers (plurality of tiers or stages) in a direction (height direction) perpendicular to the surface of the base member 10 as shown in FIG. 7B. The raised or bulged wave-like structure can be utilized as it is as a concave-convex pattern of an optical substrate such as a diffraction grating or the like. Accordingly, unlike the case of phase separation brought about by the thermal annealing, there is no need to remove one of the homopolymers by means of the etching after the phase separation. Note that a vertical cylinder structure or a spherical structure may be included in a part of the horizontal cylinder structure.

As conceptually shown in FIG. 7A, the surface shape, which is defined by the polymer segment 34 by means of the solvent annealing process, is composed of relatively smooth and sloped (inclined) surfaces, and the surface shape forms a wave-like shape in a direction upward from the base member (referred to as "wave-like shape" in this patent application as appropriate). In the case of the wave-like shape as described above, there is no overhang. The metal layer, which is accumulated on the wave-like structure 38a as described above, is subjected to the duplication (replication) into a reversed pattern (inverted pattern) thereof, and hence the metal layer is easily releasable (peelable).

In the solvent annealing process, it is unnecessary to perform the etching process and the second heating step described above. Therefore, it is possible to simplify the substrate manufacturing (preparation) process. Further, the etching process involves such a problem that the dirt and the dust easily appear on the substrate due to the use of the etching solution and the removal of one of the homopolymers. However, the etching process is unnecessary owing to the solvent annealing process, and hence the foregoing problem is dissolved as well. It is possible to obtain the substrate on which any foreign matter scarcely adheres.

Further, it is also allowable to apply the heating process to the concave-convex structure of the thin film 38a obtained by the solvent annealing process. The wave-like concave-convex structure has been already formed by the solvent annealing process. Therefore, the heating process sometimes loosens the formed concave-convex structure, and the heating process is not necessarily indispensable. The heating process is sometimes effective when any protrusion is formed on a part of the surface of the concave-convex structure after the solvent annealing process on account of any cause or when it is intended to adjust the cycle (period) and/or the height of the concave-convex structure. For example, the heating temperature can be not less than the glass transition temperatures of the first and second polymer segments 32, 34. For example, the heating temperature can be not less than the glass transition temperatures of the homopolymers and not more than a temperature higher than the glass transition temperatures by 70° C. The heating process can be performed in the atmosphere of the atmospheric air by using, for example, an oven.

Thus, the base member 10, which has the mountain-like structure 38 obtained in the second heating step or the wave-like structure 38a obtained in the solvent annealing step, is the inspection objective for the inspection apparatus and the inspection method of the present invention. Further, the base member 10 is used as the maser for the transfer in the steps performed thereafter. The average pitch of the concavities and convexities to represent the mountain-like structure 38 or the wave-like structure 38a is preferably in a range of 100 nm to 1,500 nm, and more preferably 200 nm to 1,200 nm. If the average pitch of the concavities and convexities is less than the lower limit, then the pitch is too small with respect to the wavelength of the visible light, and hence the diffraction of the visible light, which is required for the diffraction grating obtained by using such a master block (mold), is hardly caused. If the average pitch exceeds the upper limit, then the diffraction angle of the diffraction grating obtained by using such a master block (mold) is decreased, and it is impossible to sufficiently exhibit the function as the diffraction grating. The average pitch of the concavities and convexities can be determined as follows. An arbitrary measurement area of 3 μm square (length: 3 μm, width 3 μm) or 10 μm square (length: 10 μm, width 10 μm) of a diffraction grating is measured by using an atomic force microscope to obtain a concavity-convexity analysis image. The flat processing including the primary inclination correction is applied to the obtained concavity-convexity analysis image, and then the two-dimensional high speed Fourier transform processing is applied. Thus, a Fourier transform image is obtained. The distance (unit: $\mu m^{-1}$) from the origin of the Fourier transform image and the intensity are determined for each point of the Fourier transform image. Subsequently, the average value of intensities is obtained for the points positioned at an identical distance. The relationship between the distance from the origin of the Fourier transform image and the average value of intensities determined as described above is plotted. The fitting is effected by using a spline function. The wave number, at which the intensity provides the peak, is regarded as the average wave number ($\mu m^{-1}$), and the reciprocal thereof is obtained to be regarded as the average pitch. Alternatively, it is also allowable that the average pitch is obtained in accordance with another method. For example, an arbitrary measurement area of 3 μm square (length: 3 μm, width 3 μm) or 10 μm square (length: 10 μm, width 10 μm) of a diffraction grating is measured to obtain a concavity-convexity analysis image. Not less than 100 spacing distances are measured between arbitrary adjoining convexities or between arbitrary adjoining concavities in the concavity-convexity analysis image, and an average thereof is calculated to determine the average pitch of the concavity and convexity.

The Fourier transform image provides a circular motif or marking (pattern) formed approximately about the center of the origin for which the absolute value of the wave number is 0 $\mu m^{-1}$. Further, the circular motif exists in the region (area) in which the absolute value of the wave number is not more than 10 $\mu m^{-1}$ (more preferably in a range of 0.667 $\mu m^{-1}$ to 10 $\mu m^{-1}$ and much more preferably in a range of 0.833 $\mu m^{-1}$ to 5 $\mu m^{-1}$). The circular motif of the Fourier transform image is the motif observed by assembling or gathering the bright spots in the Fourier transform image. The term "circular" referred to herein means the fact that the motif obtained by assembling or gathering the bright spots seems to have an approximately circular shape, which is the concept including those in which a part of the outer shape is convex or concave as well. The motif obtained by assembling or gathering the bright spots seems to be approximately annular in some cases. In this case, the shape is expressed as "annular shape". Note that the "annular shape" resides in the concept which includes those in which the shapes of the outer circle and the inner circle of the ring seem to have approximately circular shapes and which also includes those in which parts of the outer shapes of the outer circle and the inner circle of the ring as described above seem to be convex or concave. Further, the phrase "circular or annular motif exists in the region (area) in which the absolute value of the wave number is not more than 10 $\mu m^{-1}$ (more preferably in a range of 0.667 $\mu m^{-1}$ to 10 $\mu m^{-1}$ and much more preferably in a range of 0.833 $\mu m^{-1}$ to 5 $\mu m^{-1}$)" refers to the fact that the bright spots of not less than 30% (more preferably not less than 50%, much more preferably not less than 80%, and especially preferably not less than 90%) of the bright spots for constructing the Fourier transform image exist in the region (area) in which the absolute value of the wave number is not more than 10 $\mu m^{-1}$ (more preferably in a range of 0.667 to 10 $\mu m^{-1}$ and much more preferably in a range of 0.833 $\mu m^{-1}$ to 5 $\mu m^{-1}$). Note that the following fact has been revealed about the relationship between the pattern of the concave-convex structure and the Fourier transform image. When the concave-convex structure itself has neither the pitch distribution nor the directivity, the Fourier transform image also appears as a random pattern (having no motif). However, when the concave-convex structure is isotropic as a whole in the XY directions but the pitch involves the distribution, then a circular or annular Fourier transform image appears. When the concave-convex structure has the single pitch, there is such a tendency that the annular ring, which appears on the Fourier transform image, becomes sharp.

The two-dimensional high speed Fourier transform process for the concavity-convexity analysis image can be performed with ease by means of the electronic image processing by using a computer provided with software of the two-dimensional high speed Fourier transform process.

The average height (depth) of the concavities and convexities to represent the mountain-like structure 38 or the wave-like structure 38*a* is preferably in a range of 20 nm to 200 nm and more preferably in a range of 30 nm to 150 nm. If the average height of the concavities and convexities is less than the lower limit, then the height is insufficient with respect to the wavelength of the visible light, and hence the diffraction becomes insufficient. If the average height of the concavities and convexities exceeds the upper limit, the electric field distribution in an EL layer becomes nonuniform when the obtained diffraction grating is utilized as an optical element disposed on the light extraction port side of an organic EL element. The element is easily destroyed by the heat generated by the concentration of the electric field on the specified portion, and the service life tends to become short. Note that the average height of the concavity and convexity refers to the average value of the depth distribution of the concavity and convexity when the height of the concavity and convexity (distance in the depth direction between the concavity and the convexity) is measured on the surface of the mountain-like structure 38 or the wave-like structure 38*a*. Further, the following value is adopted for the average value of the depth distribution of the concavity and convexity as described above. That is, the value is calculated such that the concavity-convexity analysis image is measured by using a scanning probe microscope (for example, product name: "E-sweep" produced by SII Nanotechnology Inc.) in relation to the shape of the concavity and convexity of the surface, and then not less than 100 distances in the depth direction, each of which is provided between an arbitrary concavity and an arbitrary convexity, are measured in the concavity-convexity analysis image as described above so that an average thereof is determined.

[Seed Layer Forming Step and Electroforming Step]

Figure 8A:
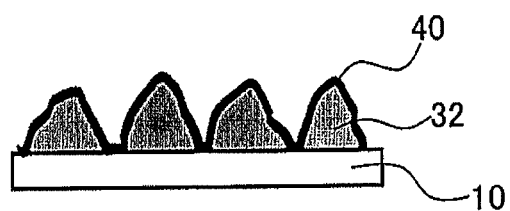
FIGS. 8A to 8D conceptually show the process for manufacturing a metal substrate having a concave-convex structure by means of electroforming.

As shown in FIG. 8A, a seed layer 40, which functions as an electroconductive layer for a subsequent electroforming process, is formed on the surface of mountain-like structure 38 of the master obtained in the second heating step as described above or the wave-like structure 38*a* obtained in the solvent annealing step. The seed layer 40 can be formed by the non-electrolytic plating, sputtering, or vapor deposition.

Figure 6D:
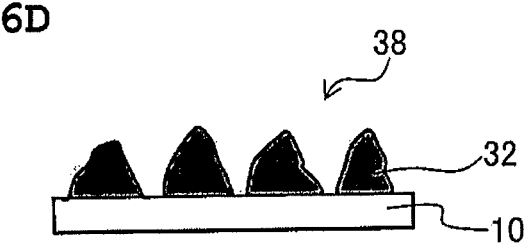

The thickness of the seed layer 40 is preferably not less than 10 nm and more preferably not less than 20 nm in order to uniformize the current density during the subsequent electroforming process so that the thickness of the metal layer accumulated by the subsequent electroforming process is made constant. As the material of the seed layer, it is possible to use, for example, nickel, copper, gold, silver, platinum, titanium, cobalt, tin, zinc, chromium, gold-cobalt alloy, gold-nickel alloy, boron-nickel alloy, solder, copper-nickel-chromium alloy, tin-nickel alloy, nickel-palladium alloy, nickel-cobalt-phosphorus alloy, or alloy thereof. Note that the seed layer is considered to adhere with a uniform thickness without any leakage owing to the mountain-like or wave-like relatively smooth structure as shown in FIG. 6D or FIGS. 7A and 7B as compared with the complicated cross-sectional structure as shown in FIG. 6C.

Figure 8B:
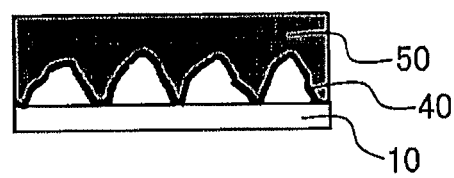

Subsequently, a metal layer 50 is accumulated on the seed layer 40 by means of the electroforming (electroplating), as shown in FIG. 8B. The whole thickness of the metal layer 50 including the thickness of the seed layer 40 can be, for example, in a range of 10 μm to 3,000 μm. As the material of the metal layer 50 to be accumulated by the electroforming, it is possible to use any of metal species as described above which can be used as the seed layer 40. Nickel is preferred in view of the wear resistance and the releasing (exfoliation or peeling off) property as the mold of the metal substrate. In this case, nickel is also preferably used for the seed layer 40. The current density during the electroforming may be, for example, in a range of 0.03 A/cm$^2$ to 10 A/cm$^2$ for suppressing bridge to form a uniform metal layer and in view of shortening of electroforming time (duration of electroforming time). Considering the easiness for performing the subsequent processes such as pressing with respect to a resin layer, releasing (exfoliation or peeling off), and cleaning (washing), the formed metal layer 50 desirably has appropriate hardness and thickness. A diamond like carbon (DLC) processing or a Cr plating processing treatment may be carried out on the surface of the metal layer in order to improve the hardness of the metal layer formed by the electroforming. Alternatively, the surface hardness of the metal layer may be improved or raised by further performing the heating process of the metal layer.

[Releasing (Exfoliation or Peeling Off) Step]

The metal layer 50 including the seed layer 40 obtained as described above is released (exfoliated or peeled off) from the base member having the concave-convex structure to thereby obtain a metal substrate to serve as a father (father die). As the releasing method (exfoliating or peeling method), the metal layer 50 may be released or exfoliated physically, or the first homopolymer and the remaining block copolymer may be dissolved and removed by using an organic solvent which dissolves the first homopolymer and the remaining block copolymer, such as toluene, tetrahydrofuran (THF), and chloroform.

[Cleaning (Washing) Step]

Figure 8C:
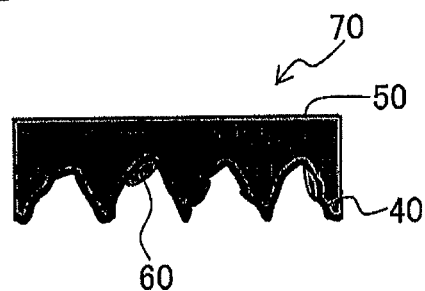
Figure 8D:
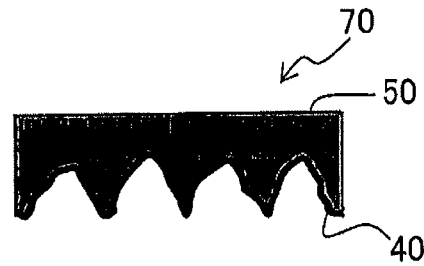

In a case of releasing the metal substrate 70 from the base member 10 having the mountain-like structure 38 or the wave-like structure 38a as described above, a polymer portion or portions 60 of the polymer such as the first polymer segment and/or the second polymer segment remains) on the metal substrate 70 in some cases, as shown in FIG. 8C. In such a case, the remaining portion or portions 60 can be removed by cleaning (washing). As a cleaning method, the wet cleaning or the dry cleaning can be used. As for the wet cleaning, the remaining portion or portions 60 can be removed by performing, for example, the cleaning with an organic solvent such as toluene and tetrahydrofuran, a surfactant, or an alkaline solution. In a case that the organic solvent is used, ultrasonic cleaning may be carried out. Alternatively, the remaining portion or portions 60 may be removed by performing the electrolytic cleaning. As for the dry cleaning, the remaining portion or portions 60 can be removed by means of the ashing by using ultraviolet light and/or plasma. The wet cleaning and the dry cleaning may be used in combination. After the cleaning as described above, a rinse process may be performed with pure water or purified water, and then ozone irradiation may be carried out after being dried. Thus, a metal substrate (mold) 70 having a desired concave-convex structure is obtained (FIG. 8D). The metal substrate 70 is provided as the light non-transmissive substrate which is the inspection objective for the inspection apparatus and the inspection method of the present invention.

Next, a method for producing a diffraction grating usable for the organic EL element, etc., by using the obtained metal substrate 70 will be explained with reference to FIGS. 9A to 9E.

[Mold-Release Treatment Step for Metal Substrate]

Figure 9A:
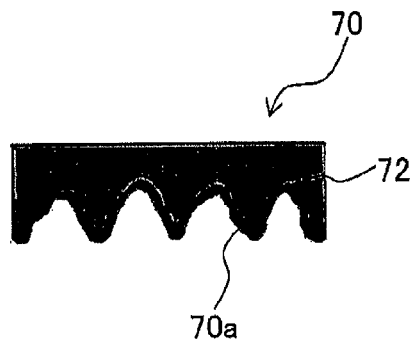
FIGS. 9A to 9E conceptually show the process for manufacturing a diffraction grating from a metal substrate having a concave-convex structure.

In a case that the metal substrate 70 as the mold is used to transfer the concave-convex structure thereof to a resin, a mold-release treatment may be performed for the metal substrate 70 in order to improve the releasability from the resin. As for the mold-release treatment, a manner or procedure to decrease the surface energy is generally used. Although the mold-release treatment is not particularly limited, the mold-release treatment includes, for example, a method in which a concave-convex surface 70a of the metal substrate 70 is coated with a mold-release agent 72 such as a fluorine-based material and a silicone resin, as shown in FIG. 9A, a method in which the surface is subjected to a treatment by using a fluorine-based silane coupling agent, a method in which a film of diamond like carbon is formed on the surface, etc.

[Transfer Step to Resin Layer of Metal Substrate]

Figure 9D:
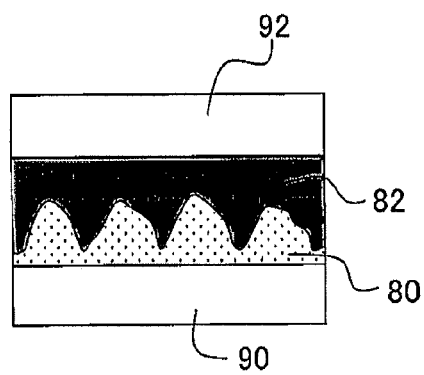
Figure 9B:
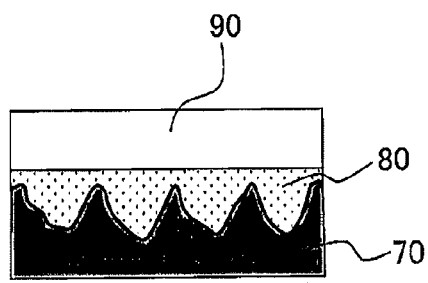

A master (mother) is produced by transferring the concave-convex structure (pattern) of the metal substrate to a resin layer 80 by using the obtained metal substrate 70. As the method of the transfer process, for example, a transparent supporting substrate 90 is coated with a curable resin, and then the resin layer 80 is cured while pressing the concave-convex structure of the metal substrate 70 against the resin layer 80, as shown in FIG. 9B. Examples of the transparent supporting substrate 90 include a base member composed of a transparent inorganic material such as glass; a base member composed of a resin such as polyethylene terephthalate (PET), polyethylene terenaphthalate (PEN), polycarbonate (PC), cycloolefin polymer (COP), polymethyl methacrylate (PMMA) or polystyrene (PS); a stacked base member having a gas barrier layer composed of an inorganic substance such as SiN, SiO$_2$, SiC, SiOxNy, TiO$_2$, or Al$_2$O$_3$ formed on the surface of a base member composed of any one of the foregoing resins; and a stacked base member formed by alternately stacking a base member composed of any one of the foregoing resins and a gas barrier layer composed of any one of the foregoing inorganic substances. Further, the thickness of the transparent supporting substrate may be in a range of 1 μm to 500 μm.

The curable resin can be exemplified, for example, by resins such as photocurable resins, thermosetting resins, moisture curing type resins, and chemical curing type resins (two-liquid mixing type resins). Specifically, the curable resin can be exemplified, for example, by various resins including, for example, monomers, oligomers, and polymers of those based on epoxy, acrylic, methacrylic, vinyl ether, oxetane, urethane, melamine, urea, polyester, polyolefin, phenol, cross-linking type liquid crystal, fluorine, silicone, and polyamide. The thickness of the curable resin is preferably in a range of 0.5 μm to 500 μm. In a case that the thickness is less than the lower limit, heights of the concavities and convexities formed on the surface of the cured resin layer are more likely to be insufficient. In a case that the thickness exceeds the upper limit, the influence of volume change of the resin which occurs upon curing is likely to be so large that the formation of the shape of the concavities and convexities tends to be unsatisfactory.

As a method for coating the transparent supporting substrate 90 with the curable resin, for example, it is possible to adopt various coating methods such as the spin coating method, spray coating method, dip coating method, dropping method, gravure printing method, screen printing method, relief printing method, die coating method, curtain coating method, ink-jet method, and sputtering method. Further, the condition for curing the curable resin varies depending on the kind of the resin to be used. However, for example, the curing temperature is preferably in a range of room temperature to 250° C., and the curing time is preferably in a range of 0.5 minute to 3 hours. Alternatively, a method may be employed in which the curable resin is cured by being irradiated with energy ray such as ultraviolet light or electron beam. In such a case, the amount of the irradiation is preferably in a range of 20 $mJ/cm^2$ to 5 $J/cm^2$.

Figure 9E:
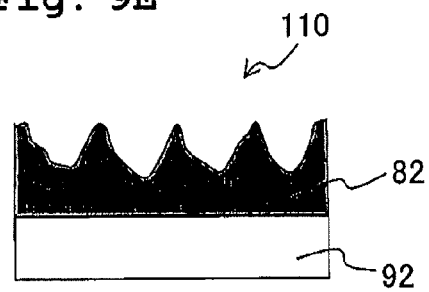
Figure 9C:
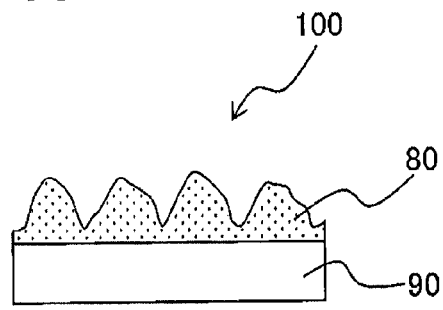

Subsequently, the metal substrate 70 is detached from the curable rein layer 80 after the curing. The method for detaching the metal substrate 70 is not limited to a mechanical releasing (exfoliating or peeling off) method, and any known arbitrary method can be adopted. Then, as shown in FIG. 9C, it is possible to obtain a resin film structure 100 having the cured rein layer 80 in which the concavities and convexities are formed on the transparent supporting substrate 90. The resin film structure 100 may be used, as it is, as the diffraction grating. The resin film structure 100 is the inspection objective for the inspection apparatus and the inspection method of the present invention, as provided as the light transmissive substrate.

The substrate production method based on the BCP method can be used not only for producing a diffraction grating provided on the light extraction port side of the organic EL element but also for producing an optical component having a minute or fine pattern usable for various devices. For example, the substrate production method based on the BCP method can be used to produce a wire grid polarizer, an antireflection film, or an optical element for providing the light confinement effect in a solar cell by being placed or installed on the photoelectric conversion surface side of the solar cell.

Thus, the resin film structure 100 having a desired pattern can be obtained. When the inverted pattern of the resin film structure 100 is used as the diffraction grating, then the resin film structure 100 obtained by performing the transfer process for the metal substrate as described above is used as the master (mother), another transparent supporting substrate 92 is coated with a curable resin layer 82, and the resin film structure 100 is pressed against the curable resin layer 82 to cure the curable resin layer 82, as shown in FIG. 9D, in the same manner as a case in which the resin film structure 100 is manufactured. Subsequently, the resin film structure 100 is released (exfoliated or peeled off) from the curable resin layer 82 which has been cured, and thus a replica 110 as another resin film structure as shown in FIG. 9E can be obtained. Further, it is allowable to produce a replica having the inverted pattern of the replica 110 by carrying out the transfer step described above by using the replica 110 as a master block, and/or it is allowable to form a sub-replica by repeating the transfer step described above again by using the replica having the inverted pattern as the master block. The replica 110 and the sub-replica as described above also have the irregular concave-convex patterns on the surfaces, and hence they are the inspection objective for the inspection apparatus and the inspection method of the present invention.

Next, an explanation will be made about a method for manufacturing or preparing a structure having concavities and convexities composed of a sol-gel material (hereinafter referred to as "sol-gel structure" or "sol-gel material substrate" as appropriate) by further using the obtained resin film structure 100 as the master block. A substrate-forming method for forming a substrate having a concave-convex pattern by using the sol-gel material mainly includes: a solution preparation step for preparing a sol solution; a coating step (application step) for applying the prepared sol solution onto a substrate (coating the substrate with the prepared sol solution); a drying step for drying a coating film of the sol solution with which the substrate is coated; a pressing step for pressing a mold having a transfer pattern formed thereon; a pre-baking (pre-calcination) step for subjecting the coating film pressed with the mold to the pre-baking, a releasing (exfoliation or peeling off) step for releasing (exfoliating or peeling off) the mold from the coating film; and a main baking (main calcination) step for subjecting the coating film to main baking. In the following, each of the steps will be explained sequentially.

At first, a sol solution is prepared to form a coating film to which a pattern is to be transferred by means of the sol-gel method (solution preparation step). For example, in a case that silica is synthesized by means of the sol-gel method on the substrate, a sol solution of metal alkoxide (silica precursor) is prepared. The silica precursor is exemplified by metal alkoxides including, for example, tetraalkoxide monomers such as tetramethoxysilane (TMOS), tetraethoxysilane (TEOS), tetra-i-propoxysilane, tetra-n-propoxysilane, tetra-t-butoxysilane, tetra-n-butoxysilane, tetra-sec-butoxysilane, and tetra-t-butoxysilane; trialkoxide monomers such as methyltrimethoxysilane, ethyltrimethoxysilane, propyltrimethoxysilane, isopropyltrimethoxysilane, phenyltrimethoxysilane, methyltriethoxysilane(MTES), ethyltriethoxysilane, propyltriethoxysilane, isopropyltriethoxysilane, phenyltriethoxysilane, methyltripropoxysilane, ethyltripropoxysilane, propyltripropoxysilane, isopropyltripropoxysilane, phenyltripropoxysilane, methyltriisopropoxysilane, ethyltriisopropoxysilane, propyltriisopropoxysilane, isopropyltriisopropoxysilane, phenyltriisopropoxysilane, and tolyltriethoxysilane; dialkoxide monomers represented by dialkoxysilanes such as dimethyldimethoxysilane, dimethyldiethoxysilane, dimethyldipropoxysilane, dimethyldiisopropoxysilane, dimethyl-di-n-butoxysilane, dimethyl-di-i-butoxysilane, dimethyl-di-sec-butoxysilane, dimethyl-di-t-butoxysilane, diethyldimethoxysilane, diethyldiethoxysilane, diethyldipropoxysilane, diethyldiisopropoxysilane, diethyl-di-n-butoxysilane, diethyl-di-i-butoxysilane, diethyl-di-sec-butoxysilane, diethyl-di-t-butoxysilane, dipropyldimethoxysilane, dipropyldiethoxysilane, dipropyldipropoxysilane, dipropyldiisopropoxysilane, dipropyl-di-n-butoxysilane, dipropyl-di-i-butoxysilane, dipropyl-di-sec-butoxysilane, dipropyl-di-t-butoxysilane, diisopropyldimethoxysilane, diisopropyldiethoxysilane, diisopropyldipropoxysilane, diisopropyldiisopropoxysilane, diisopropyl-di-n-butoxysilane, diisopropyl-di-i-butoxysilane, diisopropyl-di-sec-butoxysilane, diisopropyl-di-t-butoxysilane, diphenyldimethoxysilane, diphenyldiethoxysilane, diphenyldipropoxysilane, diphenyldiisopropoxysilane, diphenyl-di-n-butoxysilane, diphenyl-di-i-butoxysilane, diphenyl-di-sec-butoxysilane, and diphenyl-di-t-butoxysilane; monomers having vinyl group such as vinyltrimethoxysilane and vinyltriethoxysilane; monomers having epoxy group such as 2-(3,4-epoxycyclohexyl)ethyltrimethoxysilane, 3-glycidoxypropylmethyldimethoxysilane, 3-glycidoxypropyltrimethoxysilane, 3-glycidoxypropylmethyldiethoxysilane, and 3-glycidoxypropyltriethoxysilane; monomers having styryl group such as p-styryltrimethoxysilane; monomers having methacrylic group such as 3-methacryloxypropylmethyldimethoxysilane, 3-methacryloxypropyltrimethoxysilane, 3-methacryloxypropylmethyldiethoxysilane, and 3-methacryloxypropyltriethoxysilane; monomers having acrylic group such as 3-acryloxypropyltrimethoxysilane; monomers having amino group such as N-2-(aminoethyl)-3-aminopropylmethyldimethoxysilane, N-2-(aminoethyl)-3-aminopropyltrimethoxysilane, 3-aminopropyltrimethoxysilane, 3-aminopropyltriethoxysilane, 3-triethoxysilyl-N-(1,3-dimethyl-butylidene)propylamine, and N-phenyl-3-aminopropyltrimethoxysilane; monomer having ureide group such as 3-ureidepropyltriethoxysilane; monomers having mercapto group such as 3-mercaptopropylmethyldimethoxysilane and 3-mercaptopropyltrimethoxysilane; monomers having sulfide group such as bis(triethoxysilylpropyl)tetrasulfide; monomers having isocyanate group such as 3-isocyanatopropyltriethoxysilane; polymers obtained by polymerizing the foregoing monomers in small amounts; and composite materials characterized in that functional group and/or polymer is/are introduced into a part of the material as described above. Further, a part of or all of the alkyl group and the phenyl group may be substituted with fluorine. Further, examples of the silica precursor include metal acetylacetonate, metal carboxylate, oxychloride, chloride, and mixtures thereof. The silica precursor, however, is not limited thereto. In addition to Si, examples of the metal species include Ti, Sn, Al, Zn, Zr, In, and mixtures thereof, but are not limited thereto. It is also possible to use any appropriate mixture of precursors of the oxides of the foregoing metals. Further, a hydrophobization treatment may be performed on the surface thereof. Any known method may be used as a method for the hydrophobization treatment. For example, in the case of the silica surface, the hydrophobization treatment can be performed, for example, with dimethyldichlorosilane or trimethylalkoxysilane. It is also allowable to use a method in which the hydrophobization treatment is performed with silicone oil and trimethylsilylating agent such as hexamethyldisilazane. It is also allowable to use a surface treatment method for metal oxide powder based on the use of supercritical carbon dioxide. Further, it is possible to use, as the silica precursor, a silane coupling agent having, in its molecule, a hydrolysis group having the affinity and the reactivity with silica and an organic functional group having the water-repellence. For example, there are exemplified silane monomer such as n-octyltriethoxysilane, methyltriethoxysilane, and methyltrimethoxysilane; vinylsilane such as vinlytriethoxysilane, vinyltrimethoxysilane, vinyltris(2-methoxyethoxy)silane, and vinylmethyldimethoxysilane; methacrylsilane such as 3-methacryloxypropyltriethoxysilane, and 3-methacryloxypropyltrimethoxysilane; epoxysilane such as 2-(3,4-epoxycyclohexyl)ethyltrimethoxysilane, 3-glycidoxypropyltrimethoxysilane, and 3-glycidoxypropyltriethoxysilane; mercaptosilane such as 3-mercaptopropyltrimethoxysilane and 3-mereaptopropyltriethoxysilane; sulfursilane such as 3-octanoylthio-1-propyltriethoxysilane; aminosilane such as 3-aminopropyltriethoxysilane, 3-aminopropyltrimethoxysilane, N-(2-aminoethyl)-3-aminopropyltrimethoxysilane, N-(2-aminoethyl)-3-aminopropylmethyldimethoxysilane, and 3-(N-phenyl)-aminopropyltrimethoxysilane; and polymers obtained by polymerizing the monomers as described above.

In a case that a mixture of TEOS and MTES is used, the mixture ratio thereof can be 1:1, for example, in a molar ratio. This sol solution produces amorphous silica by performing the hydrolysis and the polycondensation reaction. An acid such as hydrochloric acid or an alkali such as ammonia is added in order to adjust the pH of the solution as a synthesis condition. The pH is preferably not more than 4 or not less than 10. Further, water may be added in order to perform the hydrolysis. The amount of water to be added can be not less than 1.5 times that of metal alkoxide species, in the molar ratio. As for the sol-gel material, it is possible to use a material other than silica. For example, a material such as a Ti-based material, ITO (indium-tin oxide)-based material, $Al_2O_3$, $ZrO_2$, ZnO, etc., may be used.

Examples of the solvent include alcohols such as methanol, ethanol, isopropyl alcohol (IPA), and butanol; aliphatic hydrocarbons such as hexane, heptane, octane, decane, and cyclohexane; aromatic hydrocarbons such as benzene, toluene, xylene, and mesitylene; ethers such as diethyl ether, tetrahydrofuran, and dioxane; ketones such as acetone, methyl ethyl ketone, isophorone, and cyclohexanone; ether alcohols such as butoxyethyl ether, hexyloxyethyl alcohol, methoxy-2-propanol, and benzyloxyethanol; glycols such as ethylene glycol and propylene glycol; glycol ethers such as ethylene glycol dimethyl ether, diethylene glycol dimethyl ether, and propylene glycol monomethyl ether acetate; esters such as ethyl acetate, ethyl lactate, and γ-butyrolactone; phenols such as phenol and chlorophenol; amides such as N,N-dimethylformamide, N,N-dimethylacetamide, and N-methylpyrrolidone; halogen-based solvents such as chloroform, methylene chloride, tetrachloroethane, monochlorobenzene, and dichlorobenzene; hetero element-containing compounds such as carbon disulfide; water; and mixture solvents thereof. Especially, ethanol and isopropyl alcohol are preferred, and it is also preferable to use those obtained by mixing them with water.

As an additive, it is possible to use, for example, polyethylene glycol, polyethylene oxide, hydroxypropylcellulose, and polyvinyl alcohol for viscosity adjustment; alkanolamine such as triethanolamine, β-diketone such as acetylacetone, β-ketoester, formamide, dimethylformamide, and dioxane as a solution stabilizer.

The substrate is coated with the sol solution prepared as described above (coating step). It is allowable to use, as the substrate, substrates made of inorganic materials such as glass, silica glass, and silicon substrates, or substrates made of resins such as polyethylene terephthalate (PET), polyethylene terenaphthalate (PEN), polycarbonate (PC), cycloolefin polymer (COP), polymethyl methacrylate (PMMA), polystyrene (PS), polyimide (PI), and polyarylate. The substrate may be either transparent or opaque. In a case that a concave-convex patterned substrate obtained by using this substrate is to be used for producing an organic EL element as described later on, this substrate preferably is a substrate having the heat resistance and the light resistance against the UV light, etc. In view of this fact, the substrates composed of the inorganic materials such as the glass, silica glass and silicon substrates are more preferred. It is allowable to perform a surface treatment or provide an easy-adhesion layer on the substrate in order to improve the adhesion property, and it is allowable to provide a gas barrier layer in order to keep out moisture and/or gas such as oxygen. As for the coating method, it is possible to use any arbitrary coating method including, for example, the bar coating method, the spin coating method, the spray coating method, the dip coating method, the die coating method, and the ink-jet method. However, in view of the fact that the substrate having a relatively large areal size can be uniformly coated with the sol solution, and the coating can be completed quickly before the sol solution forms a gel, it is preferable to use the bar coating method, the die coating method, and the spin coating method. Note that a desired concave-convex pattern is formed with the sol-gel material layer in a subsequent or following step, and thus the surface of the substrate (including the surface treatment or the easy-adhesion layer in case that the surface treatment has been performed or the easy-adhesion layer has been formed) may be flat, while the substrate itself does not have the desired concave-convex pattern.

After the coating step, the substrate is kept (held) in the atmospheric air or under reduced pressure in order to evaporate the solvent contained in the applied coating film (hereinafter also referred to as "sol-gel material layer" as appropriate) (drying step). Subsequently, the resin film structure 100 (mold) is pressed against the coating film (pressing step). In this procedure, it is also allowable that the resin film structure 100 is pressed by using a pressing roll. In the roll process, the following advantages are obtained as compared with the press system. That is, the period of time during which the mold and the coating film are brought in contact with each other is short, and hence it is possible to prevent any deformation or collapse of pattern which would be otherwise caused by the difference in coefficient of thermal expansion among the mold, the substrate, and a stage in which the substrate is placed, etc. It is possible to prevent the generation of bubbles of gas in the pattern which would be otherwise caused by the bumping of the solvent in the gel solution and/or it is possible to prevent any trace or mark of gas from remaining. It is possible to decrease the transfer pressure and the releasing force (exfoliation or peeling force) owing to the line contact with the substrate (coating film). It is easy to deal with those having larger areas (areal sizes). No bubble is caught and included during the pressing. Further, it is also allowable to perform the heating while allowing the resin film structure 100 to be pressed.

After the resin film structure 100 as the mold is pressed against the coating film (sol-gel material layer), the coating film may be subjected to the pre-baking (pre-calcination) (pre-baking step). The pre-baking promotes the gelation of the coating film to solidify the pattern, thereby making the pattern be less likely to be collapsed during the releasing or exfoliation. In a case that the pre-baking is performed, the heating is preferably performed at a temperature in a range of 40° C. to 150° C. in the atmospheric air. It is not necessarily indispensable to perform the pre-baking.

The resin film structure 100 is released (exfoliated) from the coating film (sol-gel material layer) after the pressing step or the pre-baking step. When the roll is used during the pressing procedure, it is enough that the releasing (exfoliation) force is small as compared with any plate-shaped mold. The mold can be easily released (exfoliated) from the coating film without allowing the coating film to remain on the mold.

After the resin film structure 100 is peeled off (exfoliated) from the coating film (sol-gel material layer) on the substrate, the coating film is subjected to the main baking (main calcination) (main baking step). The hydroxyl group or the like contained in silica (amorphous silica) for constructing the coating film is eliminated (subjected to the leaving) by the main baking, and the coating film is further strengthened. The main baking may be performed at a temperature in a range of 200° C. to 1200° C. for a duration of time about in a range of 5 minutes to 6 hours. In such a manner, the coating film is cured, and a sol-gel structure (diffraction grating) provided with a concave-convex pattern film which corresponds to the concave-convex pattern of the resin film structure 100 is obtained, namely a sol-gel structure (diffraction grating) in which the sol-gel material layer having the irregular concave-convex pattern is directly formed on the flat substrate is obtained. In this situation, silica as the sol-gel material layer is amorphous, crystalline, or in a mixture state of the amorphous and the crystalline, depending on the baking temperature and the baking time. The sol-gel structure obtained as described above is also the inspection objective for the inspection apparatus and the inspection method of the present invention.

In a case that the replica 110 (or sol-gel structure) is to be duplicated by using the resin film structure 100, or in a case that still another replica (or sol-gel structure) is to be duplicated by using the obtained replica 110 (or sol-gel structure), a film may be stacked on the surface of the resin film structure 100 or the replica 110 having the concave-convex pattern formed thereon, by means of a gas phase method such as the vapor deposition method or the sputtering method. By stacking the film as described above, in a case that transfer etc. is performed, for example, by coating the surface thereof with the resin, the adhesion with respect to the resin (for example, a UV curable resin) can be lowered so as to allow the master block to be peeled off more easily. Examples of the vapor-deposited film as described above include metals such as aluminum, gold, silver, platinum, and nickel; and metal oxides such as aluminum oxide. Further, the thickness of such a film is preferably in a range of 5 nm to 500 nm. In a case that the thickness is less than the lower limit, a uniform film is difficult to be obtained, and thus the effect of sufficiently lowering the adhesion is decreased. In a case that the thickness exceeds the upper limit, the shape of the master block is more likely to be blunt or dull (loosened). In a case that the cured resin layer of the resin film structure 100 or the replica 110 is composed of a UV curable resin, postcure may be conducted as appropriate, for example, by performing the irradiation with ultraviolet light again after the resin has been cured.

Furthermore, in the steps shown in FIGS. 9B and 9D, the curable resins 80, 82 are applied onto the transparent supporting substrates 90, 92 respectively. It is allowable, however, to use a master block obtained by applying the curable resin directly onto the surface of the metal substrate 70 which is the original master block or onto the surface of the cured resin layer 80, curing the applied curable resin, and detaching the curable resin after being cured. Alternatively, instead of coating the surface of the master block with the resin, it is allowable to press the master block against a coating film of the resin so that the concave-convex film of the cured resin obtained by curing the resin is used as the master block.

B. Method for Producing Substrate by BKL Method

As described in WO2011/007878A1 in detail, the BKL method comprises a step (concave-convex shape forming step) for forming concavities and convexities based on wrinkles on a surface of a vapor deposition film by forming the vapor deposition film on a surface of a polymer film composed of a polymer having the volume which changes depending on the heat under a temperature condition of not less than 70° C. and then cooling the polymer film and the vapor deposition film, and a step (master block forming step) for adhering and curing a master block material on the vapor deposition film and then detaching the master block material after the curing from the vapor deposition film to obtain a master block.

Figure 10A:
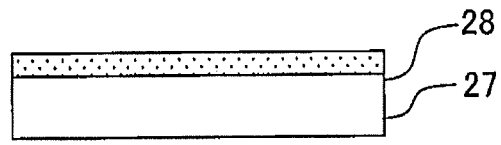
FIGS. 10A to 10D conceptually show the process for manufacturing a concave-convex structure by means of the BKL method.
Figure 10B:
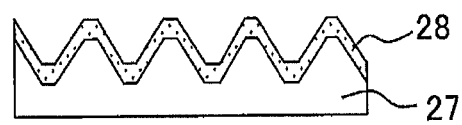
Figure 10C:
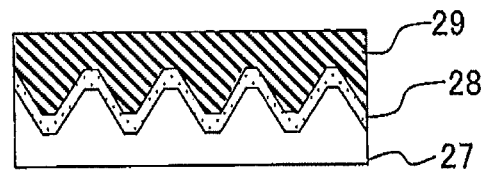

FIGS. 10A to 10D show schematic views for illustrating a preferred embodiment of the method for producing the master block in the method for producing the diffraction grating in accordance with the BKL method. FIG. 10A shows a sectional view schematically illustrating a state in which a vapor deposition film 28 is formed on a surface of a polymer film 27 in the method for producing the master block. FIG. 10B shows a sectional view schematically illustrating a state in which concavities and convexities based on wrinkles are formed on a surface of the vapor deposition film 28 by cooling the polymer film 27 and the vapor deposition film 28. FIG. 10C shows a sectional view schematically illustrating a state in which a master block material 29 is adhered and cured on the vapor deposition film 28 formed with the concavities and convexities. FIG. 1 OD shows a sectional view schematically illustrating a state in which the master block 29 after the curing is detached from the vapor deposition film 28.

In the concave-convex shape forming step, at first, the polymer film composed of a polymer having the volume which is changed depending on the heat is prepared. As for the polymer in which the volume is changed depending on the heat, it is possible to appropriately use those in which the volume is changed by means of the heating or the cooling (for example, those having the coefficient of thermal expansion of not less than 50 ppm/K). However, in view of the fact that the concavities and convexities are easily formed by the wrinkles on the surface of the vapor deposition film because the difference is large between the coefficient of thermal expansion of the polymer and the coefficient of thermal expansion of the vapor deposition film and the high flexibility is provided, it is more preferable to use silicone-based polymer, and it is especially preferable to use silicone-based polymer containing polydimethylsiloxane. As for the method for forming the polymer film as described above, it is possible to adopt, for example, the spin coating method, dip coating method, dropping method, gravure printing method, screen printing method, relief printing method, die coating method, curtain coating method, ink-jet method, spray coating method, sputtering method, vacuum vapor deposition method, etc. Further, the thickness of the polymer film as described above is preferably in a range of 10 μm to 5,000 μm and more preferably in a range of 10 μm to 2,000 μm.

Subsequently, in the concave-convex shape forming step, the vapor deposition film 28 is formed on the surface of the polymer film 27 under the temperature condition of not less than 70° C. (see FIG. 10A). It is necessary that the temperature, which is adopted when the vapor deposition film 28 is formed, should be not less than 70° C. However, it is more preferable that the temperature is not less than 90° C. If the temperature is less than 70° C., it is impossible to sufficiently form the concavities and convexities based on the wrinkles on the surface of the vapor deposition film. As for the method for forming the vapor deposition film 28, it is possible to appropriately adopt any known method include, for example, the vapor deposition method and the sputtering method. Among the method as described above, it is preferable to adopt the vapor deposition method in view of the fact that the shapes of the concavities and convexities formed on the surface of the polymer film are maintained. Further, the material of the vapor deposition film 28 is not specifically limited. However, the material is exemplified, for example, by metals such as aluminum, gold, silver, platinum, and nickel; and metal oxides such as aluminum oxide.

Subsequently, in the concave-convex shape forming step, the polymer film 27 and the vapor deposition film 28 are cooled, and thus the concavities and convexities based on the wrinkles are formed on the surface of the vapor deposition film 28 (see FIG. 10B). As described above, there is a difference between the coefficient of thermal expansion of the polymer film 27 and the coefficient of thermal expansion of the vapor deposition film 28. Therefore, the polymer film 27 and the vapor deposition film 28 as shown in FIG. 10A undergo the change of the volume caused by the heat respectively, and it is possible to form the concavities and convexities based on the winkles (so-called buckling pattern or so-called Turing pattern) on the surface of the vapor deposition film 28 as shown in FIG. 10B. Further, it is preferable that the temperatures of the polymer film 27 and the vapor deposition film 28 after the cooling are not more than 40° C. If the temperatures of the polymer film 27 and the vapor deposition film 28 after the cooling exceed the upper limit, there is such a tendency that it is difficult to form the concavities and convexities based on the winkles on the surface of the vapor deposition film. Further, it is preferable that the temperature decreasing velocity (temperature lowering velocity), which is adopted when the polymer film 27 and the vapor deposition film 28 are cooled, is in a range of 1° C./minute to 80° C./minute. If the temperature decreasing velocity is less than the lower limit, there is such a tendency that the concavities and convexities are mitigated. On the other hand, if the temperature decreasing velocity exceeds the upper limit, there is such a tendency that scratches such as cracks or the like are easily formed on the surface of the polymer film or the vapor deposition film.

In the master block forming step, at first, as shown in FIG. 10C, a master block material 29 is adhered and cured on the vapor deposition film 28. The master block material 29 as described above is not specifically limited. The master block material 29 is exemplified, for example, by inorganic substances such as nickel, silicon, silicon carbide, tantalum, glassy carbon, silica glass, and silica; and resin compositions such as silicone-based polymer (silicone rubber), urethane rubber, norbornene resin, polycarbonate, polyethylene terephthalate, polystyrene, polymethyl methacrylate, acrylic, and liquid crystal polymer. Among the master block materials 29 as described above, in view of the moldability, the fine shape following performance, and the mold release, it is more preferable to use silicone-based polymer, nickel, silicon, silicon carbide, tantalum, glassy carbon, silica glass, and silica, it is much more preferable to use silicone-based polymer, and it is especially preferable to use silicone-based polymer containing polymethylsiloxane. Further, the method for adhering the master block material 29 as described above is not specifically limited. For example, it is possible to adopt various coating methods including, for example, the vacuum vapor deposition method, spin coating method, spray coating method, dip coating method, dropping method, gravure printing method, screen printing method, relief printing method, die coating method, curtain coating method, ink jet method, and sputtering method. Further, the condition, under which the master block material 29 is cured, differs depending on the kind or type of the master block material to be used. However, for example, it is preferable that the curing temperature is in a range of room temperature to 250° C., and the curing time is in a range of 0.5 minute to 3 hours. Further, it is also allowable to adopt a method in which the curing is performed by radiating the energy ray such as ultraviolet light or electron beam. In such a case, it is preferable that the amount of irradiation is in a range of 20 mJ/cm$^2$ to 10 J/cm$^2$.

Figure 10D:
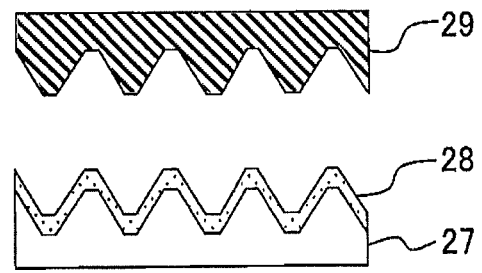

After that, in the master block forming step, as shown in FIG. 10D, the master block material 29 after the curing is detached from the vapor deposition film 28 to obtain the master block 29. The method for detaching the master block 29 from the vapor deposition film 28 is not specifically limited. It is possible to appropriately adopt any known method. The master block 29 obtained as described above is the inspection objective for the inspection apparatus and the inspection method of the present invention. Further, the substrate having the irregular concave-convex pattern on the surface obtained in the middle of the process, for example, the substrate having the buckling pattern as shown in FIG. 10B is also the inspection objective for the inspection apparatus and the inspection method of the present invention.

In the BKL method, it is also allowable that the concave-convex shape forming step and the master block forming step are repeated by using the master block 29 obtained as the polymer film. In this way, it is possible to deepen the wrinkles formed on the surface of the master block, and it is possible to increase the average height of the concavities and convexities formed on the surface of the master block.

Further, it is also allowable that a film, which is obtained by applying a resin (material used for the master block material) to the surface of the obtained master block 29, curing the resin, and then detaching the cured resin, is used as a master block. Furthermore, it is also allowable that a concave-convex film of curable resin, which is obtained by pressing the master block 29 against a coating film of resin and curing the resin in place of the application of the resin to the surface of the obtained master block 29, is used as a master block. As described above, a resin film, in which the concavities and convexities are inverted, can be also utilized as a master block.

Further, it is also allowable that a final master block is produced by repeating the inversion and the transfer of the concavities and convexities by the aid of one or more intermediate master block or master blocks as starting from the master block 29. As for the intermediate master block as described above, it is possible to utilize one obtained by appropriately inverting or transferring the concave-convex structure as described above. Furthermore, when the master block is produced by repeating the inversion and the transfer of the concavities and convexities as described above, it is also possible to once perform the transfer to a flexible material (for example, plastic film or silicone rubber), in order that the transfer of the concave-convex structure is made easy even when a substrate having no flexibility (for example, glass), with which it is difficult to release (exfoliate or peel off) the resin film or the like, is used, when the concave-convex structure of the master block is transferred. There is such a tendency that the concave-convex structure is matched with the employed master block (parity is adjusted) with ease. Moreover, it is also allowable that the intermediate master block as described above is coated with a polymer in which the volume is changed by the heat, a polymer film obtained by the curing is used as a master block 29, and the concave-convex shape forming step and the master block forming step are further repeated. Moreover, it is also allowable that when the intermediate master block is composed of UV-curable resin, then the ultraviolet light is radiated during the production to obtain an intermediate master block, and the ultraviolet light is thereafter radiated again to perform the postcure. In this way, when the master block composed of the UV-curable resin is irradiated with the ultraviolet light again to perform the postcure, then there is such a tendency that the degree of crosslinking of the master block is improved, and the mechanical strength and the chemical resistance are improved.

Further, it is also allowable that the plating process is applied to the master block (including the intermediate master block) by utilizing any known method to convert the master block into a metal mold or die. When the master block is subjected to the plating so that the master block is converted into the metal mold or die as described above, there is such a tendency that the master block, which is excellent in the mechanical strength and which is repeatedly usable, is obtained. When the master block subjected to the plating as described above is used as a mold for the nano-imprinting or the like, it is possible to mass-produce the resin substrate having a predetermined concave-convex pattern by repeatedly performing the transfer to the curable resin substrate. Materials, which can be used for the plating as described above, are exemplified, for example, by nickel, copper, iron, nickel-cobalt alloy, and nickel-iron alloy. Note that the thickness of the plating layer as described above is preferably 50 μm to 1 mm, for example, in view of the mechanical strength and the time required for manufacturing or preparing the mold.

The master block (for example, the master block 29 and the master block obtained by repeating the concave-convex shape forming step and the master block forming step by using the master block 29 obtained as the polymer film), which is obtained by carrying out the BKL method as described above, can be used as the master block for forming the diffraction grating. Further, it is also allowable that a sol-gel structure, which has concavities and convexities composed of a sol-gel material, is manufactured by further using, as the master block, the resin substrate obtained by carrying out the BKL method, in the same manner as the procedure in which the sol-gel structure having the concavities and convexities composed of the sol-gel material is manufactured by further using, as the master block, the resin film structure obtained by the BCP method.

Further, it is also allowable that a master block, which is obtained by heating the master block obtained by the BKL method for about 1 hour to 48 hours under a temperature condition of about 80° C. to 200° C., is used as the master block to be used for the production of the diffraction grating. When the master block is heated as described above, a diffraction grating is obtained, especially a diffraction grating having the concave-convex structure satisfactory for the organic EL element is obtained. The substrate (master block), which has the irregular concave-convex pattern on the surface, is obtained by carrying out the BKL method as described above. Any substrate and any sol-gel structure, which are obtained by the transfer by using the substrate as described above, are also the inspection objective for the inspection apparatus and the inspection method of the present invention.

<Method for Producing Organic EL Element>

Next, the organic EL element is produced by using the substrate which is judged to be acceptable in the judging step described above and which is included in the resin film structures (or the glass substrates or the sol-gel structures having the concavities and convexities formed with the sol-gel material) obtained by using the method as exemplified by the BCP method and the BKL method. In relation to the production method, an explanation will be made with reference to FIG. 11 about the diffraction grating composed of the resin film structure 100.

Figure 11:
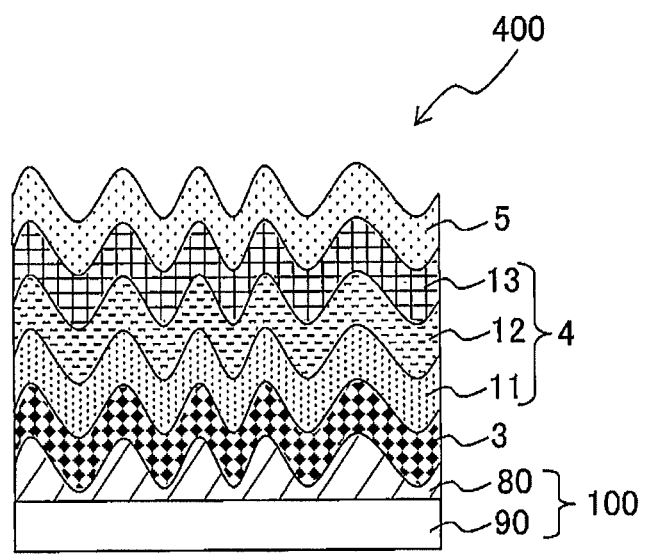
FIG. 11 shows a cross-sectional structure of an organic EL element.

At first, as shown in FIG. 11, a transparent electrode 3 is stacked on the resin layer 80 of the resin film structure 100 so as to maintain the concave-convex structure formed on the surface of the resin layer 80. Examples of those usable as the material for the transparent electrode 3 include indium oxide, zinc oxide, tin oxide, indium-tin oxide (ITO) which is a composite material thereof; gold; platinum; silver; copper, etc. Among these materials, ITO is preferred from the viewpoint of the transparency and the electrical conductivity. The thickness of the transparent electrode 3 is preferably within a range of 20 nm to 500 nm. In a case that the thickness is less than the lower limit, the electrical conductivity is more likely to be insufficient. In a case that the thickness exceeds the upper limit, there is possibility that the transparency is so insufficient that the emitted EL light cannot be extracted to the outside sufficiently. As the method for stacking the transparent electrode 3, it is possible to appropriately adopt any known method such as the vapor deposition method and sputtering method, etc. Among these methods, the sputtering method is preferably employed from the viewpoint of improving adhesion property. Note that a glass substrate may be stuck to the side opposite to the resin layer 80 of the resin film structure 100 before providing the transparent electrode 3 on the resin layer 80.

Subsequently, an organic layer 4 as shown in FIG. 11 is stacked on the transparent electrode 3 so that the concave-convex shape formed on the surface of the resin layer 80 is maintained. The organic layer 4 as described above is not particularly limited, provided that the organic layer 4 is one usable as an organic layer of the organic EL element. As the organic layer 4, any known organic layer can be used as appropriate. Further, the organic layer 4 as described above may be a stacked body of various organic thin films, and may be, for example, a stacked body composed of an anode buffer layer 11, a hole (positive hole) transporting layer 12, and an electron transporting layer 13 as shown in FIG. 11. In this context, the material for the anode buffer layer 11 is exemplified, for example, by copper phthalocyanine and PEDOT. Further, the material for the hole transporting layer 12 is exemplified, for example, by triphenylamine, triphenyldiamine derivative (TPD), benzidine, pyrazoline, styrylamine, hydrazone, triphenylmethane, carbazole, and derivatives thereof. Further, the material for the electron transporting layer 13 is exemplified, for example, by aluminum quinolinol complex (Alq), phenanthroline derivative, oxadiazole derivative, triazole derivative, phenylquinoxaline derivative, and silole derivative. The organic layer 4 as described above may be a stacked body of a hole injecting layer composed of, for example, triphenylamine derivative and a light emitting layer composed of fluorescent organic solid such as anthracene or the like, a stacked body of a light emitting layer as described above and an electron injecting layer composed of perylene derivative or the like, or a stacked body of a hole injecting layer, a light emitting layer, and an electron injecting layer as described above.

The organic layer 4 may be a stacked body composed of a hole transporting layer, a light emitting layer, and an electron transporting layer. In this case, examples of the material of the hole transporting layer include aromatic diamine compounds such as phthalocyanine derivatives, naphthalocyanine derivatives, porphyrin derivatives, N,N'-bis(3-methylphenyl)-(1,1'-biphenyl)-4,4'-diamine (TPD), and 4,4'-bis[N-(naphthyl)-N-phenyl-amino]biphenyl (α-NPD); oxazole; oxadiazole; triazole; imidazole; imidazolone; stilbene derivatives; pyrazoline derivatives; tetrahydroimidazole; polyarylalkane; butadiene; and 4,4',4''-tris(N-(3-methylphenyl)N-phenylamino)triphenylamine (m-MTDATA). The material of the hole transporting layer, however, is not limited thereto.

Further, the light emitting layer is provided so that a hole (positive hole) injected from the transparent electrode and an electron injected from a metal electrode are recombined to emit light. Examples of the material usable as the light emitting layer include: metallo-organic complex such as anthracene, naphthalene, pyrene, tetracene, coronene, perylene, phthaloperylene, naphthaloperylene, diphenylbutadiene, tetraphenylbutadiene, coumarin, oxadiazole, bisbenzoxazoline, bisstyryl, cyclopentadiene, and aluminum-quinolinol complex (Alq3); tri-(p-terphenyl-4-yl)amine; 1-aryl-2,5-di(2-thienyl) pyrrole derivatives; pyran; quinacridone; rubren; distyrylbenzene derivatives; distyryl arylene derivatives; distyryl amine derivatives; and various fluorescent pigments or dyes. Furthermore, it is also preferable that light-emitting materials selected from the foregoing compounds are mixed as appropriate and then are used. Moreover, it is possible to preferably use a material system which exhibits emission of light from a spin multiplet, such as a phosphorescence emitting material which generates emission of phosphorescence, and a compound which includes, in a part of the molecules, a constituent portion formed by the foregoing materials as well. Note that the phosphorescence emitting material preferably includes heavy metal such as iridium.

A host material having high carrier mobility may be doped with each of the foregoing light-emitting materials as a guest material to cause the light emission by utilizing the dipole-dipole interaction (Forster mechanism) or the electron exchange interaction (Dexter mechanism). Examples of the material of the electron transporting layer include heterocyclic tetracarboxylic acid anhydrides such as nitro-substituted fluorene derivatives, diphenylquinone derivatives, thiopyran dioxide derivatives, and naphthaleneperylene; and metallo-organic complex such as carbodiimide, fluorenylidene methane derivatives, anthraquinodimethane and anthrone derivatives, oxadiazole derivatives, and aluminum-quinolinol complex (Alq3). Further, in the oxadiazole derivatives described above, it is also possible to use, as an electron transporting material, thiadiazole derivatives in which oxygen atoms of oxadiazole rings are substituted by sulfur atoms and quinoxaline derivatives having quinoxaline rings known as electron attracting group (electron withdrawing group). Furthermore, it is also possible to use a polymeric (macromolecular) material in which the material as described above is introduced into a macromolecular chain or the material as described above is used as a main chain of a macromolecule. Note that the hole transporting layer or the electron transporting layer may also function as the light-emitting layer. In this case, two organic layers are provided between the transparent electrode and the metal electrode described later on.

Further, from the viewpoint of facilitating the electron injection or the hole injection into the organic layer 4 as described above, a layer composed of a metal fluoride such as lithium fluoride (LiF) or $Li_2O_3$, a highly active alkaline earth metal such as Ca, Ba, or Cs, an organic insulating material or the like may be provided on the transparent electrode 3 or the organic layer 4.

In a case that the organic layer 4 is a stacked body composed of the anode buffer layer 11, the hole transporting layer 12, and the electron transporting layer 13, the thicknesses of the anode buffer layer 11, the hole transporting layer 12, and the electron transporting layer 13 are preferably in a range of 1 nm to 50 nm, a range of 5 nm to 200 nm, and a range of 5 nm to 200 nm respectively, in view of the fact that the shapes of the concavities and convexities formed on the surface of the cured resin layer are maintained. Further, in a case that the organic layer 4 is a stacked body composed of the hole transporting layer, the light emitting layer, and the electron transporting layer, the thicknesses of the hole transporting layer, the light emitting layer, and the electron transporting layer are preferably in a range of 1 nm to 200 nm, a range of 5 nm to 100 nm, and a range of 5 nm to 200 nm respectively. As the method for stacking the organic layer 4, any known method such as the vapor deposition method, sputtering method, and die coating method can be employed as appropriate. Among the methods as described above, it is preferable to use the vapor deposition method in view of the fact that the shapes of the concavities and convexities formed on the surface of the resin layer 80 are maintained.

In the step for forming the organic EL element, subsequently, as shown in FIG. 11, a metal electrode 5 is stacked on the organic layer 4 so that the shapes of the concavities and convexities formed on the surface of the resin layer 80 are maintained. Materials of the metal electrode 5 are not particularly limited, and a substance having a small work function can be used as appropriate. Examples of the materials include aluminum, MgAg, MgIn, and AlLi. The thickness of the metal electrode 5 is preferably in a range of 50 nm to 500 nm. In a case that the thickness is less than the lower limit, the electrical conductivity is more likely to be decreased. In a case that the thickness exceeds the upper limit, there is possibility that it is difficult to maintain the concave-convex shape. Any known method such as the vapor deposition method, sputtering method, etc. can be adopted to stack the metal electrode 5. Among the methods as described above, it is preferable to use the vapor deposition method in view of the fact that the concave-convex structure formed on the surface of the resin layer 80 is maintained. Accordingly, an organic EL element 400 having a structure as shown in FIG. 11 is obtained.

The resin layer 80 of the resin film structure 100 produced by the BCP method has the mountain-like structure or the wave-like structure. Therefore, the transparent electrode 3, the organic layer 4, and the metal electrode 5 are easily stacked respectively so that the mountain-like or wave-like structure of the resist layer 80 is maintained. It is possible to sufficiently suppress such a situation that the light, which is generated by the organic layer 4, is totally reflected by the respective interfaces to repeat the multipath reflection (multiple reflection) at the inside of the element. Further, the light, which has been totally reflected by the interface between the transparent supporting substrate 90 and the air, can be allowed to outgo again in accordance with the diffraction effect. Furthermore, the transparent electrode 3, the organic layer 4, and the metal electrode 5 also easily form the structures which are the same as or similar to the mountain-like or wave-like structure formed on the surface of the resin layer 80. As a result, the distance between the electrodes of the transparent electrode 3 and the metal electrode 5 is partially shortened. Therefore, it is possible to expect the increase in the electric field intensity during the application of the voltage as compared with those in which the distance between the electrodes of the transparent electrode 3 and the metal electrode 5 is uniform. It is also possible to improve the light emission efficiency of the organic EL element.

In the diffraction grating (substrate) produced according to the substrate production method of the present invention and the organic EL element containing the same, the average height of the concavities and convexities formed on the surface of the diffraction grating (surface of the cured curable resin) is preferably in a range of 20 nm to 200 nm and more preferably in a range of 30 nm to 150 nm as described above.

In the diffraction grating (substrate) produced according to the present invention and the organic EL element containing the same, the average pitch of the concavities and convexities formed on the surface of the diffraction grating (surface of the cured curable resin) is preferably in a range of 100 nm to 1,500 nm and more preferably in a range of 200 nm to 1,200 nm as described above.

EXAMPLES

The present invention will be specifically explained below with reference to Examples and Comparative Examples. However, the present invention is not limited to Examples.

Example 1

In Example 1, a diffraction grating substrate to be used for an organic EL element is manufactured or prepared as the substrate having the irregular concave-convex surface.
<Preparation of Diffraction Grating Mold>
A block copolymer produced by Polymer Source composed of polystyrene (hereinafter referred to as "PS" as appropriate) and polymethyl methacrylate (hereinafter referred to as "PMMA" as appropriate) as described below was prepared.
Mn of PS segment=750,000;
Mn of PMMA segment=720,000;
Mn of block copolymer=1,470,000;
Volume ratio between PS segment and PMMA segment (PS:PMMA)=54:46;
Molecular weight distribution (Mw/Mn)=1.21;
Tg of PS segment=107° C.;
Tg of PMMA segment 134° C.

The volume ratio between the first polymer segment and the second polymer segment (the first polymer segment: the second polymer segment) in the block copolymer was calculated on the assumption that the density of polystyrene was 1.05 g/cm$^3$ and the density of polymethyl methacrylate was 1.19 g/cm$^3$. The number average molecular weights (Mn) and the weight average molecular weights (Mw) of polymer segments or polymers were measured by using a gel permeation chromatography (Model No.: "GPC-8020" manufactured by TOSOH CORPORATION, in which TSKgel SuperH1000, SuperH2000, SuperH3000, and SuperH4000 were connected in series). The glass transition temperatures (Tg) of the polymer segments were measured by using a differential scanning calorimeter (manufactured by PERKIN-ELMER, INC, under the product name of "DSC7"), while the temperature was raised at a rate of temperature rise of 20° C./min over a temperature range of 0° C. to 200° C. The solubility parameters of polystyrene and polymethyl methacrylate were 9.0 and 9.3 respectively (see "Kagaku Binran Ouyou Hen" (Handbook of Chemistry, Applied Chemistry), 2nd edition).

Toluene was added to 150 mg of the block copolymer and 45 mg of Polyethylene Glycol 2050 manufactured by ALDRICH (average Mn=2,050) as polyethylene oxide so that the total amount thereof was 15 g, followed by being dissolved.

The solution of the block copolymer was filtered through a membrane filter having a pore diameter of 0.5 μm to obtain a block copolymer solution. A glass substrate was coated with a mixed solution containing 1 g of KBM-5103 manufactured by SHIN-ETSU SILICONE (SHIN-ETSU CHEMICAL, CO., LTD.), 1 g of ion-exchanged water, 0.1 ml of acetic acid, and 19 g of isopropyl alcohol, by means of the spin coating (which was performed for 10 seconds with rotation speed of 500 rpm, and then performed continuously for 45 seconds with rotation speed of 800 rpm). The treatment was performed for 15 minutes at 130°, and thus a silane coupling treated glass was obtained. The silane coupling treated glass as the base member was coated with the obtained block copolymer solution by means of the spin coat to provide a film thickness in a range of 150 nm to 170 nm. The spin coat was performed for 10 seconds at a rotation speed of 200 rpm and then was performed for 30 seconds at a rotation speed of 300 rpm.

Then, the base member on which the thin film was formed was stationarily placed in a desiccator, filled in advance with chloroform vapor, at room temperature for 24 hours, and thus the solvent annealing process was applied. Inside the desiccator (volume: 5 L), a screw-type container charged with 100 g of chloroform was placed, and the atmosphere inside the desiccator was filled with chloroform at the saturated vapor pressure. Concavities and convexities were observed on the surface of the thin film after the solvent annealing process, and it was found that the block copolymer for forming the thin film underwent the micro phase separation. The cross section of the thin film was observed by using a transmission electron microscope (TEM) (H-7100FA manufactured by HITACHI, LTD.). As a result, the circular cross section of the PS portion was aligned in two tiers (stages or rows) in a direction perpendicular to the surface of the substrate (height direction) while the circular cross sections of the PS portion were separated from each other in a direction parallel to the surface of the substrate. When considering together with an analysis image obtained by using an atomic force microscope, it was revealed that the PS portion was subjected to the phase separation to form a horizontal cylinder structure from the PMMA portion. A state was given, in which the PS portion existing as the core (island) was surrounded by the PMMA portion (sea). Thus, the thin film was obtained, which had the wave-like form in accordance with the solvent annealing process.

The concave-convex shape on the surface of the thin film, which was made to have the wave-like shape by the solvent annealing process (at a stage before the electroforming), was observed by using an atomic force microscope (a scanning probe microscope equipped with an environment control unit "Nanonavi II Station/E-sweep" manufactured by Hitachi High Tech Science Corporation). As calculated from the concavity and convexity analysis image of the thin film surface, the average pitch of the concave-convex pattern was 305 nm, the average value (m) of the depth (height) of the concavity and convexity was 78.1 nm, the standard deviation ($\sigma$) of the depth distribution of the concavity and convexity was 24.7 nm, and the kurtosis of the concavity and convexity was −0.63. Analysis conditions of the atomic force microscope were as follows.

Measurement mode: dynamic force mode
Cantilever: SI-DF40P2 (material: Si, lever width: 40 µm, diameter of tip of chip: 10 nm)
Measurement atmosphere: in atmospheric air
Measurement temperature: 25° C.

About 20 nm of a thin nickel layer was formed as a current seed layer by performing the sputtering on the surface of the thin film processed to have the wave-like shape by means of the solvent annealing process as described above. Subsequently, the base member equipped with the thin film was immersed in a nickel sulfamate bath and subjected to an electroforming process (maximum current density: 0.05 A/cm$^2$) at a temperature of 50° C. so as to precipitate nickel until the thickness became 250 µm. The base member equipped with the thin film was mechanically peeled off or released from the nickel electroforming body obtained as described above. Subsequently, the nickel electroforming body was immersed in a tetrahydrofuran solvent for 2 hours, and then the nickel electroforming body was coated with an acrylic-based UV curable resin, followed by being cured and peeled off. This process was repeated three times, and thus polymer component(s) adhered to a part of the surface of the electroforming body was (were) removed. After that, the nickel electroforming body was immersed in Chemisol 2303 manufactured by THE JAPAN CEE-BEE CHEMICAL CO., LTD., and was cleaned or washed while being stirred or agitated for 2 hours at 50° C. Thereafter, the UV ozone treatment was applied to the nickel electroforming body for 10 minutes.

Subsequently, the nickel electroforming body was immersed in HD-2101TH manufactured by DAIKIN CHEMICALS SALES, CO., LTD. for about 1 minute and was dried, and then stationarily placed overnight. The next day, the nickel electroforming body was immersed in HDTH manufactured by DAIKIN CHEMICALS SALES, CO., LTD. and was subjected to an ultrasonic cleaning (washing) process for about 1 minute. In such a manner, a nickel mold for which a mold-release treatment had been performed was obtained.

The shape of the concavities and convexities on the surface of the nickel electroforming body was observed by using the atomic force microscope described above. The analysis condition of the atomic force microscope is the same as or equivalent to that described above. The average height of the concavities and convexities of the thin film surface and the standard deviation of the height (depth) of the concavities and convexities, which were calculated from the concavity and convexity analysis image of the surface of the nickel electroforming body, were 45.7 nm and 22.4 nm respectively.

Subsequently, a resin substrate provided with a concave-convex pattern was produced or manufactured by using the nickel electroforming body as the mold, in the following manner. A PET substrate (COSMOSHINE A-4100 manufactured by TOYOBO CO., LTD.) was coated with a fluorine-based UV curable resin. The fluorine-based UV curable resin was cured by irradiation with ultraviolet light at 600 mJ/cm$^2$ while the nickel mold was pressed thereagainst. After curing of the resin, the nickel mold was exfoliated or peeled off from the cured resin. Accordingly, a diffraction grating, which was composed of a resin substrate with the concave-convex pattern to which the surface profile (surface shape) of the nickel mold was transferred, was obtained. The resin substrate with the concave-convex pattern can be used as it is as a diffraction grating. In Example 1, however, this resin substrate with the concave-convex pattern was used again as a mold (diffraction grating mold) to thereby produce or manufacture a diffraction grating in the following manner.

2.5 g of tetraethoxysilane (TEOS) and 2.1 g of methyltriethoxysilane (MTES) were added dropwise to a mixture solution of 24.3 g of ethanol, 2.16 g of water, and 0.0094 g of concentrated hydrochloric acid, followed by being stirred or agitated for 2 hours at a temperature of 23° C. and a humidity of 45% to obtain a sol solution. The sol solution was applied onto a glass plate made of soda-lime of 15×15×0.11 cm by means of the bar coating. Doctor Blade (manufactured by YOSHIMITSU SEIKI CO., LTD.) was used as a bar coater. The doctor blade was designed so that the film thickness of a coating film was 5 µm. However, the doctor blade was adjusted so that the film thickness of a coating film was 40 µm by sticking an imide tape having a thickness of 35 µm to the doctor blade. When 60 seconds elapsed after the application, the diffraction grating mold was pressed against the coating film on the glass plate by using a pressing roll in accordance with a method described below.

At first, the surface of the diffraction grating mold, which was formed with the pattern, was pressed against the coating film on the glass substrate while the pressing roll at 23° C. was rotated from one end to the other end of the glass substrate. Immediately after the completion of pressing, the substrate was moved onto a hot plate, and the substrate was heated at 100° C. (pre-baking). After the heating was continued for 5 minutes, the substrate was removed from the hot plate, and the diffraction grating mold was manually detached (exfoliated or peeled off) from the substrate from the edge. The diffraction grating mold was peeled off such that an angle (peel angle) of the diffraction grating mold with respect to the substrate was about 30°. Subsequently, the main baking was performed by heating the substrate at 300° C. for 60 minutes by using an oven. Thus, a diffraction grating formed with the concave-convex pattern composed of the sol-gel material was obtained.

The micro inspection and the macro inspection were performed by using the inspection apparatus 102 shown in FIG. 2 for the substrate having the thin film allowed to have the wave-like shape by the solvent annealing process for the thin film of the block copolymer (hereinafter referred to as "BCP thin film substrate" as appropriate), the nickel mold subjected to the mold release process, the resin substrate with the concave-convex pattern (diffraction grating mold), and the diffraction grating formed with the concave-convex pattern composed of the sol-gel material (hereinafter referred to as "sol-gel material substrate" as appropriate) obtained as described above.

A white LED bar illumination having an areal size of a light emitting part of 21 mm×300 mm (LNSP-300SW produced by CCS CORPORATION) was used as the transmitting light illumination for micro 124 in the micro inspection unit 106 of the inspection apparatus 102 shown in FIG. 2, and the illumination was installed at a position of 20 mm under or below the transport surface of the transport system 108. Further, a white LED bar illumination having an areal size of a light emitting part of 21 mm×500 mm (LNSP-500SW produced by CCS Corporation) was used as the non-transmitting light illumination for micro 126, and the illumination was installed at a position of 120 mm over or above the transport surface of the transport system 108. Four CCD cameras of 15 µm/pixel (TL7400-CL produced by Takenaka System Co., Ltd.) were used as the micro cameras 122, and the CCD cameras were installed at positions of 65 mm over or above the transport surface of the transport system 108. The distance between the micro cameras was 105 mm. A high directivity LED bar illumination having a light emission center wavelength of 460 nm and an areal size of a light emitting part of 12 mm×600 mm (LND-600H-BL produced by CCS Corporation) was used as the transmitting light illumination for macro 114 in the macro inspection unit 104 of the inspection apparatus 102, and the illumination was installed at a position of 20 mm under or below the transport surface of the transport system 108. Further, a high directivity LED bar illumination having a light emission center wavelength of 460 nm and an areal size of a light emitting part of 12 mm×600 mm (LND-600H-BL produced by CCS Corporation) was used as the non-transmitting light illumination for macro 116, and the illumination was installed at a position of 120 mm over or above the transport surface of the transport system 108. One CCD camera of 80 µm/pixel (S3-20-02K40 produced by DALSA Inc.) was used as the macro camera 112, and the CCD camera was installed at a position of 425 mm over or above the transport surface of the transport system 108.

<Inspection of BCP Thin Film Substrate>

The apparatus was installed so that the angle of incidence of the light into the BCP thin film substrate at the micro inspection position MI of the transmitting light illumination for micro 124, the light receiving angle from the BCP thin film substrate at the micro inspection position MI of the micro camera 122, the angle of incidence of the light into the BCP thin film substrate at the macro inspection position MA of the transmitting light illumination for macro 114, and the light receiving angle from the BCP thin film substrate at the macro inspection position MA of the macro camera 112 were 40°, 60°, 40°, and 60° respectively. The BCP thin film substrate having a size of 420 mm×520 mm and a thickness of 2.1 mm was installed at the transport unit 108 of the inspection apparatus 102. The transmitting light illumination for micro 124 was allowed to effect light emission at an output of 100 W for each, while transporting the BCP thin film substrate in the +Y direction at a velocity of 30 mm/s. The BCP thin film substrate was photographed by using the micro cameras 122. After that, the transmitting light illumination for macro 114 was allowed to effect light emission at an output of 27 W for each, while transporting the BCP thin film substrate in the −Y direction on the transport unit 108 at a velocity of 130 mm/s, and the BCP thin film substrate was photographed by using the macro camera 112. The image pickup frequencies of the micro camera 122 and the macro camera 112 were 2,000 Hz and 1,625 Hz respectively. Further, the gain adjustment was performed before the photographing so that each of the pixel values of the micro camera 122 and the macro camera 112 at the micro inspection position MI and the macro inspection position MA was a half of the maximum of 256, i.e., about 128. The bottom-hat processing was applied to the obtained image fed from the micro camera 122 by means of the control system 111, and the macro unevenness correction was applied thereto. After that, the luminance value was evaluated. A part or portion was judged to be a defect if the areal size of the portion in which the luminance value was not more than 90% or not less than 120% of the average luminance value of the entire screen was not less than 900 µm². Further, the luminance value of the obtained image fed from the macro camera 112 was evaluated by means of the control system 111. If the areal size of a portion in which the pixel value was not more than 80% or not less than 120% as compared with the pixel value of a non-defective portion was less than 1 mm², the product was judged to be a non-defective product having no luminance unevenness. If the areal size was not less than 1 mm², the product was judged to be a defective product having any luminance unevenness. As a result of the micro inspection, 108 defects (dark defects) in each of which the luminance value was not more than 80% of the average luminance value of the entire screen and 13 defects (bright defects) in each of which the luminance value was not less than 120% of the average luminance value of the entire screen were present. The results of the macro inspection were within the normal range in relation to the entire area.

<Inspection of Nickel Mold>

The apparatus was installed so that the angle of incidence of the light into the nickel mold at the micro inspection position MI of the non-transmitting light illumination for micro 126, the light receiving angle from the nickel mold at the micro inspection position MI of the micro camera 122, the angle of incidence of the light into the nickel mold at the macro inspection position MA of the non-transmitting light illumination for macro 116, and the light receiving angle from the nickel mold at the macro inspection position MA of the macro camera 112 were 30°, 60°, 30°, and 60° respectively. The nickel mold having a size of 400 mm×500 mm and a thickness of 0.3 mm was installed at the transport unit 108 of the inspection apparatus 102. The non-transmitting light illumination for micro 126 was allowed to effect light emission at an output of 100 W for each, while transporting the nickel mold in the +Y direction at a velocity of 30 mm/s. The nickel mold was photographed by using the micro cameras 122. After that, the non-transmitting light illumination for macro 116 was allowed to effect light emission at an output of 27 W for each, while transporting the nickel mold in the −Y direction on the transport unit 108 at a velocity of 130 mm/s, and the nickel mold was photographed by using the macro camera 112. The image pickup frequencies of the micro camera 122 and the macro camera 112 were 2,000 Hz and 1,625 Hz respectively. Further, the gain adjustment was performed before the photographing so that each of the pixel values of the micro camera 122 and the macro camera 112 at the micro inspection position MI and the macro inspection position MA was a half of the maximum of 256, i.e., about 128. The bottom-hat processing was applied to the obtained image fed from the micro camera 122 by means of the control system 111, and the macro unevenness correction was applied thereto. After that, the luminance value was evaluated. A part or portion was judged to be a defect if the areal size of the portion in which the luminance value was not more than 90% or not less than 120% of the average luminance value of the entire screen was not less than 900 µm². Further, the luminance value of the obtained image fed from the macro camera 112 was evaluated by means of the control system 111. If the areal size of a portion in which the pixel value was not more than 80% or not less than 120% as compared with the pixel value of a non-defective portion was less than 1 mm², the product was judged to be a non-defective product. If the areal size was not less than 1 mm², the product was judged to be a defective product. As a result of the micro inspection, 128 defects (dark defects) in each of which the luminance value was not more than 80% of the average luminance value of the entire screen and 4 defects (bright defects) in each of which the luminance value was not less than 120% of the average luminance value of the entire screen were present. The results of the macro inspection were within the normal range in relation to the entire area.

<Inspection of Diffraction Grating Mold>

The apparatus was installed so that the angle of incidence of the light into the diffraction grating mold at the micro inspection position MI of the transmitting light illumination for micro 124, the light receiving angle from the diffraction grating mold at the micro inspection position MI of the micro camera 122, the angle of incidence of the light into the diffraction grating mold at the macro inspection position MA of the transmitting light illumination for macro 114, and the light receiving angle from the diffraction grating mold at the macro inspection position MA of the macro camera 112 were 40°, 60°, 40°, and 60° respectively. The diffraction grating mold having a size of 400 mm×500 mm and a thickness of 0.1 mm was installed at the transport unit 108 of the inspection apparatus 102. The transmitting light illumination for micro 124 was allowed to effect light emission at an output of 100 W for each, while transporting the diffraction grating mold in the +Y direction at a velocity of 30 mm/s. The diffraction grating mold was photographed by using the micro cameras 122. After that, the transmitting light illumination for macro 114 was allowed to effect light emission at an output of 27 W for each, while transporting the diffraction grating mold in the −Y direction on the transport unit 108 at a velocity of 130 mm/s, and the diffraction grating mold was photographed by using the macro camera 112. The image pickup frequencies of the micro camera 122 and the macro camera 112 were 2,000 Hz and 1,625 Hz respectively. Further, the gain adjustment was performed before the photographing so that each of the pixel values of the micro camera 122 and the macro camera 112 at the micro inspection position MI and the macro inspection position MA was a half of the maximum of 256, i.e., about 128. The bottom-hat processing was applied to the obtained image fed from the micro camera 122 by means of the control system 111, and the macro unevenness correction was applied thereto. After that, the luminance value was evaluated. A part or portion was judged to be a defect if the areal size of the portion in which the luminance value was not more than 90% or not less than 120% of the average luminance value of the entire screen was not less than 900 µm². Further, the luminance value of the obtained image fed from the macro camera 112 was evaluated by means of the control system 111. If the areal size of a portion in which the pixel value was not more than 80% or not less than 120% as compared with the pixel value of a non-defective portion was less than 1 mm², the product was judged to be a non-defective product. If the areal size was not less than 1 mm², the product was judged to be a defective product. As a result of the micro inspection, 145 defects (dark defects) in each of which the luminance value was not more than 80% of the average luminance value of the entire screen and 53 defects (bright defects) in each of which the luminance value was not less than 120% of the average luminance value of the entire screen were present. The results of the macro inspection were within the normal range in relation to the entire area.

<Inspection of Sol-Gel Material Substrate>

The apparatus was installed so that the angle of incidence of the light into the sol-gel material substrate at the micro inspection position MI of the transmitting light illumination for micro 124, the light receiving angle from the sol-gel material substrate at the micro inspection position MI of the micro camera 122, the angle of incidence of the light into the diffraction grating mold at the macro inspection position MA of the transmitting light illumination for macro 114, and the light receiving angle from the sol-gel material substrate at the macro inspection position MA of the macro camera 112 were 40°, 60°, 40°, and 60° respectively. The sol-gel material substrate having a size of 400 mm×500 mm and a thickness of 0.7 mm was installed at the transport unit 108 of the inspection apparatus 102. The transmitting light illumination for micro 124 was allowed to effect light emission at a certain output (100 W for each), while transporting the sol-gel material substrate in the +Y direction at a velocity of 30 mm/s. The sol-gel material substrate was photographed by using the micro cameras 122. After that, the transmitting light illumination for macro 114 was allowed to effect light emission at an output of 27 W for each, while transporting the sol-gel material substrate in the −Y direction on the transport unit 108 at a velocity of 130 mm/s, and the sol-gel material substrate was photographed by using the macro camera 112. The image pickup frequencies of the micro camera 122 and the macro camera 112 were 2,000 Hz and 1,625 Hz respectively. Further, the gain adjustment was performed before the photographing so that each of the pixel values of the micro camera 122 and the macro camera 112 at the micro inspection position MI and the macro inspection position MA was a half of the maximum of 256, i.e., about 128. The macro unevenness correction based on the bottom-hat processing was applied to the obtained image fed from the micro camera 122 by means of the control system 111. After that, the luminance value was evaluated. A part or portion was judged to be a defect if the areal size of the portion in which the luminance value was not more than 90% or not less than 120% of the average luminance value of the entire screen was not less than 900 µm². Further, the luminance value of the obtained image fed from the macro camera 112 was evaluated by means of the control system 111. If the areal size of a portion in which the pixel value was not more than 80% or not less than 120% as compared with the pixel value of a non-defective portion was less than 1 mm², the product was judged to be a non-defective product. If the areal size was not less than 1 mm², the product was judged to be a defective product. As a result of the micro inspection, 183 defects (dark defects) in each of which the luminance value was not more than 80% of the average luminance value of the entire screen and 54 defects (bright defects) in each of which the luminance value was not less than 120% of the average luminance value of the entire screen were present. The results of the macro inspection were within the normal range in relation to the entire area.

Example 2

The micro inspection and the macro inspection were performed in the same manner as Example 1 by using the nickel mold manufactured in Example 1 except that the angle of incidence of the light into the nickel mold at the micro inspection position MI of the non-transmitting light illumination for micro 126 and the light receiving angle from the nickel mold at the micro inspection position MI of the micro camera 122 were changed. Further, the visual observation inspection was performed by using the nickel mold such that if any abnormal part or portion having an areal size of not less than about 900 $\mu m^2$ was present, the portion was regarded as a defect. The defect position obtained by the micro inspection based on the use of the inspection apparatus 102 was compared with the defect position obtained by the visual observation inspection. When both of the angle of incidence of the light of the non-transmitting light illumination for micro 126 and the light receiving angle of the micro camera 122 were 60°, the defect positions were scarcely coincident with each other between the inspection by the inspection apparatus and the visual observation inspection. On the other hand, when the angle of incidence of the light of the non-transmitting light illumination for micro 126 and the light receiving angle of the micro camera 122 were 30° and 60° respectively, then 31 defects were detected by only the inspection by the inspection apparatus, 26 defects were detected by only the visual observation inspection, but 195 defects were detected by both of the inspection by the inspection apparatus and the visual observation inspection. According to this fact, it is appreciated that the inspection, which reflects the actual defects, is performed when the angle of incidence of the light of the non-transmitting light illumination for micro 126 and the light receiving angle of the micro camera 122 are 30° and 60° respectively. In relation thereto, when both of the angle of incidence of the light of the non-transmitting light illumination for micro 126 and the light receiving angle of the micro camera 122 are 60°, almost all of the light coming into the camera is the regular reflection (specular reflection) light. In this case, if any foreign matter or the like exists, then the matter appears as the dark defect portion, and hence it is impossible to distinguish the pattern defect from the foreign matter. On the other hand, when the angle of incidence of the light of the non-transmitting light illumination for micro 126 and the light receiving angle of the micro camera 122 are 30° and 60° respectively, the light coming into the camera is the diffracted light or the scattered light. The camera does not receive the regular reflection light, and hence it is possible to detect only the pattern defect as the dark defect portion. The defects, which were detected when the angle of incidence of the light of the non-transmitting light illumination for micro 126 and the light receiving angle of the micro camera 122 were 30° and 60° respectively, were coincident with the defects which were grasped by the visual observation inspection.

Example 3

The micro inspection and the macro inspect were performed by using the diffraction grating mold manufactured in Example 1 in the same manner as Example 1 except that the angle of incidence of the light of the transmitting light illumination for micro 124 and the light receiving angle of the micro camera 122 were changed to angles shown in Table 1. Table 1 shows the pixel value of the normal portion in the micro inspection and the peak levels (value obtained by dividing the pixel value of the defect portion by the pixel value of the normal portion) of a perfect circular pattern defect portion of 64 µmφ (defect 1) and a perfect circular pattern defect portion of 82 µmφ (defect 2). In order to detect the defect 1 and the defect 2 as the defects, it is necessary that the pixel value of the normal portion should be not less than 120 and the peak levels of the defect 1 and the defect 2 should be not more than 90%. On condition that the angle of incidence of the light of the transmitting light illumination for micro 124 was 40° and the light receiving angle of the micro camera 122 was 60°, then the pixel value of the normal portion was 133, and the peak levels of the defect 1 and the defect 2 were 88% and 82% respectively. It was possible to detect the defect 1 and the defect 2. It is considered that the reason, why the peak level differs depending on the angle of incidence and the light receiving angle as described above, is that the diffraction and scattering effect caused by the concavities and convexities differs depending on the angle of incidence and the light receiving angle and the light receiving amount also differs thereby.

TABLE 1

| Angle of incidence of illumination light [°] | Light receiving angle of camera [°] | Pixel value of normal portion | Peak level [%] Defect 1 | Peak level [%] Defect 2 |
|---|---|---|---|---|
| 10 | 45 | 28 | — | — |
| 35 | 45 | 46 | 87 | 88 |
| 45 | 45 | 60 | 83 | 83 |
| 48 | 45 | 70 | 83 | 85 |
| 40 | 35 | 121 | 96 | 93 |
| 40 | 45 | 107 | 86 | 87 |
| 40 | 55 | 114 | 84 | 88 |
| 40 | 60 | 133 | 88 | 82 |
| 40 | 70 | 107 | 85 | 83 |

Example 4

Figure 12A:
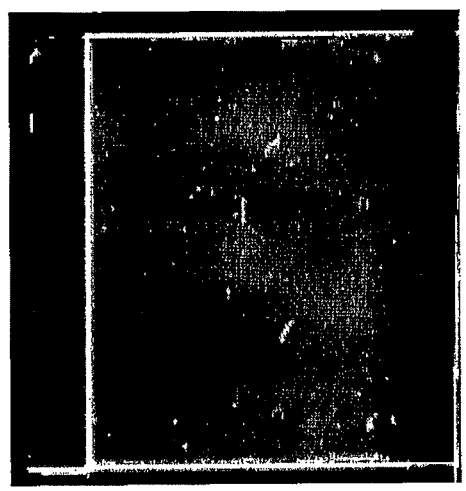
FIG. 12A shows images as results of the macro inspection for a sol-gel material substrate manufactured in Example 4 and shows a macro inspection image based on the use of an illumination having a light emission central wavelength of 460 nm.
Figure 12B:
FIG. 12B shows images as results of the macro inspection for a sol-gel material substrate manufactured in Example 4 and shows a macro inspection image based on the use of a white illumination.

The micro inspection and the macro inspection were performed by using the sol-gel material substrate manufactured in Example 1 in the same manner as Example 1 except that the transmitting light illumination for macro 114 was changed from the high directivity LED bar illumination having a light emission center wavelength of 460 nm and an areal size of a light emitting part of 12 mm×600 mm (LND-600H-BL produced by CCS Corporation) to a white LED bar illumination having an areal size of a light emitting part of 21 mm×500 mm (LNSP-500SW produced by CCS CORPORATION). FIG. 12A shows a macro inspection image of the sol-gel material substrate obtained when the illumination having the light emission center wavelength of 460 nm was used for the transmitting light illumination for macro 114 in the same manner as Example 1, and FIG. 12B shows a macro inspection image of the sol-gel material substrate obtained when the white illumination was used for the transmitting light illumination for macro 114 in Example 4. The scratches and the foreign matters were conspicuous and the unevenness of luminance was obscure in FIG. 12B as the macro inspection image based on the use of the white illuminate as compared with FIG. 12A as the macro inspection image based on the use of the illumination having the light emission center wavelength of 460 nm.

The inspection apparatus, the inspection method, and the substrate production method of the present invention have been specifically explained above with reference to Examples. However, the present invention is not limited to Examples, and it is possible to provide various changes and improvements. For example, it is also allowable to adopt the following modified embodiment of the inspection method in relation to the inspection method. In Examples described above, the amount of data for performing the image processing is larger in the micro inspection. Therefore, the inspection tact can be shortened by acquiring the data for the macro inspection during the data processing. Therefore, the micro inspection was performed antecedently, and then the macro inspection was performed. However, it is also allowable to carry out the macro inspection and the micro inspection in an order reverse thereto. Further, it is also allowable to increase the number of micro cameras 122 in order to raise the resolution of the micro inspection of the inspection apparatus 102 shown in FIG. 2. In this case, if the cameras interfere with each other, it is also allowable to arrange the plurality of cameras in a zigzag form without arranging the plurality of cameras in one array in the direction perpendicular to the transport direction. Alternatively, the resolution can be also raised in accordance with the following method without increasing the number of micro cameras 122.

Figure 13A:
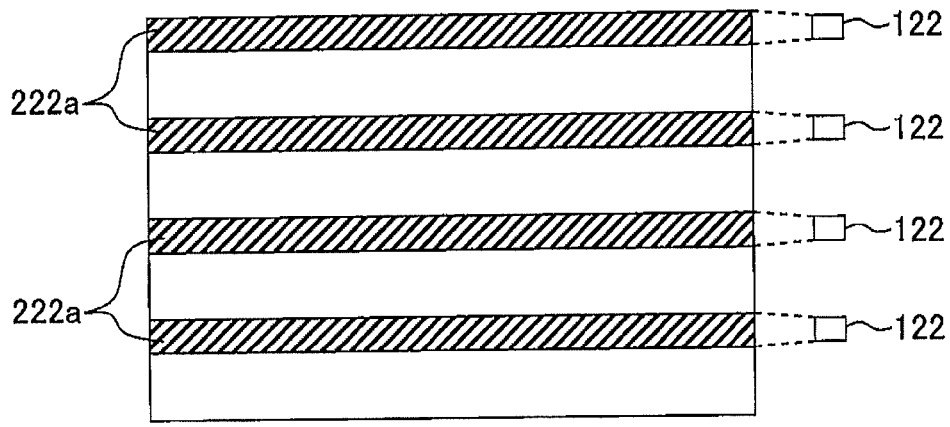
FIGS. 13A to 13C conceptually show the procedure of the micro inspection process to perform the micro inspection at a high resolution in a modified embodiment of the present invention.
Figure 13B:
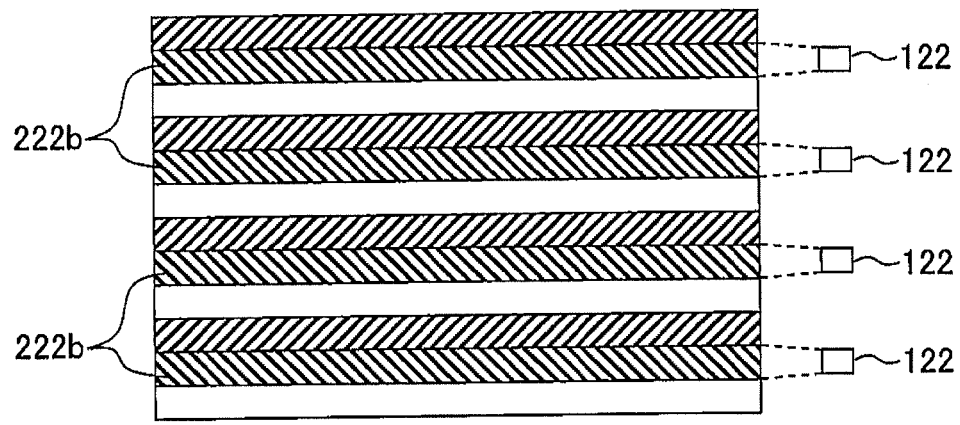
Figure 13C:
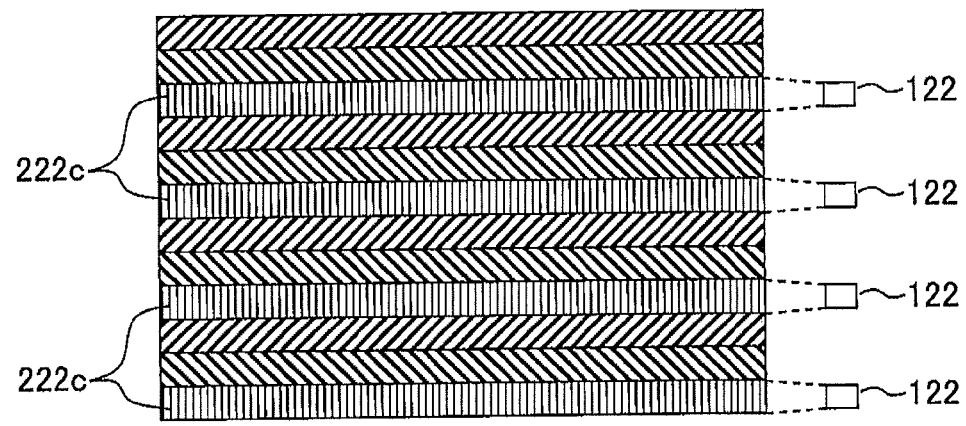

As shown in FIGS. 13A to 13C, for example, a lens (not shown), which has a resolution that is three times the resolution to be provided when the lens is not installed, is installed to each of the micro cameras 122, and thus the image pickup range of the camera is made ⅓ of that to be provided when the lens is detached. The image pickup range of the camera, which is to be provided when the lens is detached, is divided into three of a first divided area 222a, a second divided area 222b, and a third divided area 222c in a direction perpendicular to the transport direction to perform the inspection. The substrate P is transported at a transport velocity which is ⅓ of that to be provided when the lens is detached, in the +Y direction toward the micro detection position MI by using the transport system 108 (see FIG. 2). When the substrate P passes over the micro detection position MI, the scattered light, which comes from the surface of the first divided area 222a of the substrate P, is received by the four micro cameras 122. After that, the micro cameras 122 are step-moved in the X axis direction by the camera image pickup range, and then the substrate P is transported at a transport velocity of ⅓ in the −Y direction toward the micro detection position MI by using the transport system 108. When the substrate P passes over the micro inspection position MI, the scattered light, which comes from the surface of the second divided area 222b of the substrate P, is received by the four micro cameras 122. The micro cameras 122 are further step-moved in the X axis direction by the camera image pickup range, and then the substrate P is transported at a transport velocity of ⅓ in the +Y direction toward the micro detection position MI by using the transport system 108. When the substrate P passes over the micro inspection position MI, the scattered light, which comes from the surface of the third divided area 222c of the substrate P, is received by the four micro cameras 122. The intensity of the received light is inputted into the control system 111 together with the coordinate position in the transport direction of the substrate P. The light intensity, which is received from the micro inspection position MI by each of the four micro cameras 122, is allowed to correspond in relation to each of the coordinate positions (X coordinate position and Y coordinate position) of the substrate P in the image processing unit 111a. Thus, an image, which represents the intensities of the light of the entire substrate P, is synthesized by the image processing unit 111a on the basis of the light intensities of the respective position coordinates. Note that the pixel positions of the micro cameras 122 are previously allowed to correspond to the positions of the substrate P in the transport direction (Y direction) and the X direction perpendicular thereto. Accordingly, in this modified embodiment, the lens, which has the magnification that is, for example, three times that to be provided when the lens is not installed, is installed to the apparatus, and thus it is possible to obtain the resolution of the micro inspection which is three times that to be provided when the lens is detached.

According to the present invention, the substrate having the irregular concave-convex surface, which is usable for the device such as the organic EL element, can be efficiently produced, while performing the inspection for the luminance unevenness and the minute defect. Further, when the organic EL element, which has the diffraction grating substrate having the irregular concave-convex surface, is produced, then the characteristics of the luminance unevenness and the minute defect can be correlated between the organic EL element and the substrate having the irregular concave-convex surface to be used therefor, and thus it is possible to predict the occurrence of the luminance unevenness and the minute defect of the finished product and evaluate the finished product at the stage of production of the substrate. Therefore, the substrate, which is judged to be unacceptable in the judgment of the luminance unevenness and the minute defect, is excluded, and only the substrate, which is judged to be acceptable is used. Thus, the organic EL element having the uniform illuminance can be produced more reliably at a high throughput. Furthermore, even when the uniformity of the illuminance of the organic EL element is defective, it is possible to know whether the stage of occurrence of the defect is either the stage of formation of the substrate or the stage of formation of the element itself. Therefore, it is possible to respond to such a situation quickly.

What is claimed is:

1. A substrate inspection apparatus for inspecting a substrate having an irregular concave-convex surface for scattering lights, comprising:
    a first irradiation system which irradiates the substrate with a first detection light;
    a first detection system which detects any luminance unevenness from the entire concave-convex surface of the substrate irradiated with the first detection light;
    a second irradiation system which irradiates the substrate with a second detection light having a wavelength different from that of the first detection light; and
    a second detection system which detects a pattern defect of the concave-convex surface of the substrate irradiated with the second detection light.

2. The substrate inspection apparatus according to claim 1, wherein the first detection light is a blue light, and the second detection light is a white light.

3. The substrate inspection apparatus according to claim 1, wherein the first irradiation system includes a transmitting light illumination for illuminating a light transmissive substrate and a non-transmitting light illumination for illuminating a light non-transmissive substrate, and the second irradiation system includes a transmitting light illumination for illuminating the light transmissive substrate and a non-transmitting light illumination for illuminating the light non-transmissive substrate.

4. The substrate inspection apparatus according to claim 3, wherein the non-transmitting light illumination of the first irradiation system and the non-transmitting light illumination of the second irradiation system irradiate the irregular concave-convex surface of the substrate, and the transmitting light illumination of the first irradiation system and the transmitting light illumination of the second irradiation system irradiate the irregular concave-convex surface of the substrate from a surface disposed on a side opposite to the irregular concave-convex surface of the substrate.

5. The substrate inspection apparatus according to claim 3, wherein the first detection system includes a camera which detects the light coming from the light transmissive substrate illuminated with the transmitting light illumination of the first irradiation system and the light coming from the light non-transmissive substrate illuminated with the non-transmitting light illumination of the first irradiation system.

6. The substrate inspection apparatus according to claim 5, wherein the second detection system includes a camera which detects the light coming from the light transmissive substrate illuminated with the transmitting light illumination of the second irradiation system and the light coming from the light non-transmissive substrate illuminated with the non-transmitting light illumination of the second irradiation system.

7. The substrate inspection apparatus according to claim 6, wherein a resolution of the camera of the second detection system is higher than a resolution of the camera of the first detection system.

8. The substrate inspection apparatus according to claim 6, wherein the camera of the second detection system includes a plurality of cameras which detect divided areas of the substrate respectively.

9. The substrate inspection apparatus according to claim 1, wherein the first irradiation system and the second irradiation system are line-shaped illuminations extending in a predetermined direction, and the apparatus further comprises a substrate transport system which transports the substrate in a direction perpendicular to the predetermined direction.

10. The substrate inspection apparatus according to claim 9, further comprising a control system which controls the substrate transport system, the first irradiation system, the second irradiation system, the first detection system, and the second detection system, wherein the control system detects the pattern defect of the concave-convex surface when the substrate is moved by the substrate transport system in one direction with respect to the first irradiation system, the second irradiation system, the first detection system, and the second detection system, and the control system detects the luminance unevenness when the substrate is moved in a direction opposite to the one direction with respect to the first irradiation system, the second irradiation system, the first detection system, and the second detection system.

11. The substrate inspection apparatus according to claim 10, wherein the control system judges whether or not the pattern defect of the concave-convex surface and the luminance unevenness are within predetermined allowable ranges.

12. A substrate inspection method for inspecting a light non-transmissive substrate having an irregular concave-convex surface for scattering lights and a light transmissive substrate having an irregular concave-convex surface for scattering lights, the substrate inspection method comprising:
transporting the substrate with respect to a first detection system which detects any luminance unevenness from the entire concave-convex surface of the substrate and a second detector system which detects a pattern defect of the concave-convex surface of the substrate;
irradiating the concave-convex surface of the substrate with a first detection light to detect the light coming from the concave-convex surface by the first detection system, and irradiating the concave-convex surface of the substrate with a second detection light having a wavelength different from that of the first detection light to detect the light coming from the concave-convex surface by the second detection system, when the light non-transmissive substrate is transported; and
irradiating the irregular concave-convex surface of the substrate with the first detection light from a surface of the light transmissive substrate disposed on a side opposite to the concave-convex surface to detect the light coming from the concave-convex surface by the first detection system, and irradiating the irregular concave-convex surface of the substrate with the second detection light from the surface of the light transmissive substrate disposed on the opposite side to detect the light coming from the concave-convex surface by the second detection system, when the light transmissive substrate is transported.

13. The substrate inspection method according to claim 12, wherein the first detection light is a blue light, and the second detection light is a white light.

14. The substrate inspection method according to claim 12, wherein each of the first detection light and the second detection light is irradiated by a line-shaped illumination extending in a predetermined direction, and the transport of the substrate is to transport the substrate in a direction perpendicular to the predetermined direction.

15. The substrate inspection method according to claim 12, wherein the pattern defect of the concave-convex surface of the substrate is detected when the substrate is moved in one direction with respect to the first detection system and the second detection system, and the luminance unevenness of the substrate is detected when the substrate is moved in a direction opposite to the one direction with respect to the first detection system and the second detection system.

16. The substrate inspection method according to claim 12, further comprising judging whether or not the pattern defect of the concave-convex surface and the luminance unevenness are within predetermined allowable ranges.

17. A substrate production method for producing a substrate having an irregular concave-convex surface for scattering lights, comprising:
preparing the substrate having the irregular concave-convex surface; and
inspecting the substrate having the irregular concave-convex surface by using the substrate inspection method as defined in any one of claim 12.

18. The substrate production method according to claim 17, wherein the preparation of the substrate having the irregular concave-convex surface comprises preparing a light non-transmissive substrate having an irregular concave-convex pattern, and transferring the irregular concave-convex pattern of the light non-transmissive substrate.

19. The substrate production method according to claim 17, wherein the preparation of the substrate having the irregular concave-convex surface comprises utilizing phase separation of a block copolymer.

20. The substrate production method according to claim 17, wherein the irregular concave-convex surface is formed of a metal, resin, or sol-gel material.

21. A method for producing an organic electroluminescent element, comprising preparing a diffraction grating substrate having a concave-convex surface by the substrate production method as defined in claim 17, and successively stacking a transparent electrode, an organic layer, and a metal electrode on the concave-convex surface of the diffraction grating substrate.

22. The method for producing the organic electroluminescent element according to claim 21, wherein the substrate inspection method comprises judging whether or not the pattern defect of the concave-convex surface and the luminance unevenness are within predetermined allowable ranges, and the transparent electrode, the organic layer, and the metal electrode are successively stacked on the concave-convex surface of the diffraction grating substrate only when it is judged that the luminance unevenness and the pattern defect of the prepared diffraction grating substrate are within the predetermined allowable ranges.

* * * * *